United States Patent [19]

Goff et al.

[11] Patent Number: 4,943,531

[45] Date of Patent: Jul. 24, 1990

[54] EXPRESSION OF ENZYMATICALLY ACTIVE REVERSE TRANSCRIPTASE

[75] Inventors: Stephen P. Goff, Tenafly, N.J.; Naoko Tanese, New York; Monica J. Roth, Bronx, both of N.Y.

[73] Assignee: The Trustees of Columbia University in the City of New York, New York, N.Y.

[21] Appl. No.: 731,128

[22] Filed: May 6, 1985

[51] Int. Cl.$^5$ .................. C12N 9/12; C12N 1/20; C12N 15/00
[52] U.S. Cl. .................. 435/194; 435/320; 435/252.33; 935/14
[58] Field of Search .......... 435/172.3, 194, 199, 435/240.2, 253, 255, 320, 815; 935/14, 27, 28, 29, 41, 43, 44, 45, 46, 47, 69, 72, 73

[56] References Cited

U.S. PATENT DOCUMENTS

| | | | |
|---|---|---|---|
| 4,387,162 | 6/1983 | Aigle et al. | 435/320 |
| 4,487,835 | 12/1984 | Uhlin et al. | 435/320 |
| 4,663,290 | 5/1987 | Weis et al. | 935/14 |

FOREIGN PATENT DOCUMENTS 0000380 2/1984 PCT Int'l Appl. .................. 935/14

OTHER PUBLICATIONS

Kotewicz, M. et al., *Gene*, vol. 35, pp. 249–258, 1985.
Tacon, W. et al., *Molec Gen. Genet.*, vol. 177, pp. 427–438, 1980.
Maniatis, T. et al., *Molecular Cloning*, Cold Spring Harbor Laboratory, pp. 128–129, 1982.
Marcus, S. et al., *J. Virology*, vol. 14, pp. 853–859, 1974.
Shinnick, T. et al., *Nature*, vol. 293, pp. 543–548, 1981.
Schwartzberg, P. et al., *Cell*, vol. 37, pp. 1043–1052, Jul., 1984.
Goff, S. et al., *J. Virology*, vol. 38, pp. 239–248, 1981.
Tanese, N. et al., *J. Virology*, vol. 59, pp. 328–340, Aug., 1986.
Tanese, N. et al., *Proc. Natl. Acad. Sci.*, vol. 82, pp. 4944–4948, Aug., 1985.
Roth, M. et al., *J. Biol. Chem.*, vol. 260, pp. 9326–9335, Aug., 1985.

*Primary Examiner*—Jayme A. Huleatt
*Attorney, Agent, or Firm*—John P. White

[57] ABSTRACT

This invention provides a plasmic which, when introduced into a suitable host cell and grown under appropriate conditions, effects expression of a gene on the plasmid and production of a polypeptide having reverse transcriptase activity. The plasmid is a double-stranded DNA molecule which includes in a 5' to 3' order the following: a DNA sequence which includes an inducible promoter; a DNA sequence which includes an ATG initiation condon; the central portion of the Moloney murine leukemia virus (MuLV) pol gene, said central portion including a DNA sequence which encodes the polypeptide having reverse transcriptase activity; a DNA sequence which contains a gene associated with a selectable or identifiable phenotypic trait which is manifested when the vector is present in the host cell; and a DNA sequence which contains an origin of replication from a bacterial plasmid capable of autonomous replication in the host cell.

The invention also concerns a method for recovering purified enzymatically-active polypeptide having reverse transcriptase activity, the polypeptide being encoded by the plasmid pB6 B15.23, from a suitable host cell e.g., *E. coli* HB101 producing the polypeptide. Finally, the invention concerns use of the polypeptide to prepare complementary DNA (cDNA).

3 Claims, 5 Drawing Sheets

EXPRESSION OF ENZYMATICALLY ACTIVE REVERSE TRANSCRIPTASE

BACKGROUND OF THE INVENTION

This invention was made with government Grant Number CA 30488 from the National Cancer Institute of the United States Department of Health and Human Services. The U.S. government has certain rights in this invention.

Throughout this application various publications are referenced by number within parentheses. Full citations for these publications may be found at the end of the specification immediately preceding the claims. The disclosures of these publications in their entireties are hereby incorporated by reference into this application in order to more fully describe the state of the art to which this invention pertains.

In the early stages of the retroviral life cycle, viral RNA is copied to form a double-stranded DNA, which is integrated into host DNA to generate the provirus (for review, 1). The synthesis of the proviral DNA is catalyzed by the enzyme reverse transcriptase, which may efficiently utilize either RNA or DN templates for DNA synthesis by the elongation of a primer bearing a paired 3' hydroxyl terminus. Inherent in the same protein is a second activity, RNAse H, which degrades RNA present as a duplex RNA:DNA hybrid. The viral pol encodes many enzymatic activities which participate in various steps of the life cycle. The pol gene product is initially expressed as a polyprotein Pr200$^{gag\text{-}pol}$ (2, 3), containing sequences encoded by the gag gene fused to sequences encoded by the pol gene; proteolytic processing is required to remove the gag sequences and to excise the mature products from the pol sequences.

In the murine retroviruses, such as Moloney murine leukemia virus (MuLV), the pol sequences are processed to three nonoverlapping products: a small protein encoded by the 5' end of the gene, probably the protease needed for gag and pol processing; reverse transcriptase, the largest protein from the middle portion of the precursor; and a protein at the 3' end, apparently involved in integration of the provirus.

The viral MuLV reVerse transcriptase has been purified (4,5) and shown to be a monomer (4,5) of molecular weight between 70,000 to 80,000 daltons. The purified protein was shown to have a nuclease activity (RNAse H) which degraded RNA contained in an RNA-DNA hybrid (4,5).

Reverse transcriptase is widely used as a means of producing complementary DNA (cDNA) copies of messenger RNA (mRNA) molecules. These cDNAs may be inserted into expression vectors which are used to transform cells so that the resulting cells produce a desired polypeptide encoded by the original mRNA.

The only disclosure in the art concerning production of a polypeptide having reverse transcriptase activity by bacteria transformed with genetically engineered vectors involves the shotgun cloning into *Escherichia coli* of total genomic DNA isolated from the cells of warm-blooded vertebrate animals, e.g. fowl liver cells, [Japanese patent publication No. 56087600].

Reverse transcriptase produced by and isolated from, virions is commercially available. However, it is quite expensive due to the low abundance of the pol gene product in the virions.

To overcome this problem, the present invention uses a modified region of the MuLV pol gene which is inserted into a plasmid, its transcription being controlled by an inducible promoter. The modifications to the inserted gene fragment result in the production of a polypeptide with reverse transcriptase activity.

Additionally, the present invention describes a method of isolating the non-naturally occurring polypeptide whereby a novel combination of column chromatography techniques is employed, including phosphocellulose and polyribocytidylic acid-agarose chromatography.

SUMMARY OF THE INVENTION

The invention concerns a double-stranded DNA plasmid which, when expressed in a suitable host cell, produces a polypeptide having reverse transcriptase activity, the plasmid comprising in 5' to 3' order:

a DNA sequence which includes an inducible promoter;

a DNA sequence which includes an ATG initiation codon;

the central portion of the Moloney murine leukemia virus (MuLV) pol gene, said central portion including a DNA sequence which encodes the polypeptide having reverse transcriptase activity;

a DNA sequence which contains a gene associated with a selectable or identifiable phenotypic trait which is manifested when the vector is present in the host cell; and a DNA sequence which contains an origin of replication from a bacterial plasmid capable of autonomous replication in the host cell.

The plasmid of this invention may be introduced into a suitable host cell where the gene may be expressed under suitable conditions. In a presently preferred embodiment, the plasmid is pB6B15.23 and the host cell is an *Escherichia coli* HB101 cell (deposited together under ATCC No. 39939). Suitable inducible promoters are ones which are induced when the host cell is grown in a medium deficient in one or more amino acids. One such inducible promoter is the Trp operon of *E. coli*.

The invention also concerns a method for recovering the polypeptide having reverse transcriptase activity in purified form after it is produced in the suitable host cell. The method comprises disrupting the host cells, recovering soluble material, then recovering from the soluble material the polypeptide in purified form, e.g. by chromatography on a series of chromatographic columns.

Host cells containing the plasmid of this invention have been used to produce a polypeptide having reverse transcriptase activity and characterized by being encoded by the plasmid pB6B15.23.

This invention also concerns uses of the novel polypeptide having reverse transcriptase activity. One such use comprises contacting of an RNA molecule with the polypeptide under suitable reverse transcribing conditions so as to produce a DNA molecule which is complementary to the RNA molecule.

DETAILED DESCRIPTION OF THE INVENTION

A double-stranded DNA plasmid has been made which, when expressed in a suitable host cell, produces a polypeptide having reverse transcriptase activity. The plasmid includes in 5' to 3' order: a DNA sequence which includes an inducible promoter; a DNA sequence which includes an ATG initiation codon; the central portion of the Moloney murine leukemia virus (MuLV) pol gene, said central portion including a DNA sequence which encodes the polypeptide having reverse transcriptase activity; a DNA sequence which contains a gene associated with a selectable or identifiable phenotypic trait such as drug resistance, e.g. ampicillin resistance, which is manifested when the vector is present in the host cell; and a DNA sequence which contains an origin of replication from a bacterial plasmid capable of autonomous replication in the host cell, e.g., *Escherichia coli*. In one embodiment the inducible promoter of the plasmid is one which is induced when the host cell is grown upon a medium deficient in one or more amino acids. Thus, the inducible promoter may be the Trp promoter of *Escherichia coli* and the medium deficient in the amino acid tryptophan. In another embodiment the inducible promoter is one which is induced when the host cell is subjected to increased temperature.

The ATG initiation codon of the plasmid may be derived from the coding sequence of the Trp E protein of *Escherichia coli*, e.g. a DNA sequence derived from a 54 nucleotide long sequence encoding a portion of the Trp E protein of *Esherichia coli*. In one embodiment the origin of replication is derived from pBR322.

Figure 2:
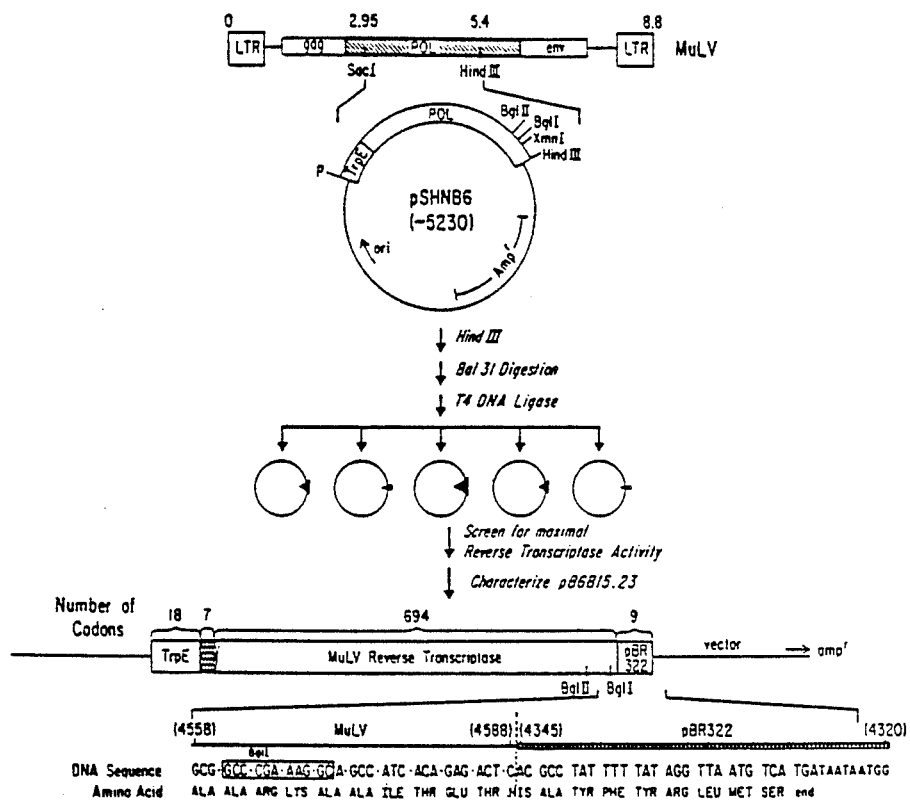
FIG. 2. Construction of plasmid pB6B15.23 expressing stable reverse transcriptase The complete genome of M-MuLV as a linear provirus is shown at the top. Long Terminal Repeats (LTRs) and the regions encoding the gag, pol, and env precursors are indicated in boxes. Plasmid pSHNB6 (6) contained the region of the pol gene from Sac I to Hind III (from 2.95 to 5.4 on the map (7)) inserted 3' of the DNA encoding the N-terminus of the trpE gene. The positions of the origin of replication (ori) and the gene conferring ampicillin resistance (amp) are indicated. pSHNB6 was linearized with Hind III, digested with Bal 31 nuclease, and ligated with T4 DNA ligase; the DNA products were used to transform HB101, and the resulting colonies were screened for reverse transcriptase as described in Experimental Procedures. The characteristics of plasmid pB6B15.23 are summarized at the bottom. The numbers in parentheses refer to the maps of M-MuLV and pBR322 as described by Sutcliffe (7 and 8, respectively). The resulting gene fusion consists of an open reading frame encoding 728 amino acids. The first 18 amino acids at the N-terminus are encoded by the trpE gene, followed by 7 amino acids which are encoded by the pol gene but are not part of the M-MuLV reverse transcriptase (S. Oroszlan, personal communication). The subsequent 694 amino acids are encoded by the pol gene, and the terminal 9 amino acids by pBR322. The sequence of the 3' terminus of the gene was determined by the method of Maxam and Gilbert (9) after 5' end labeling with polynucleotide kinase at the Bgl II site. The DNA sequence and the deduced amino acid sequence are indicated at the bottom.

The plasmid may comprise a circular double-stranded DNA sequence such as the plasmid identified as pB6B15.23, having the restriction map shown in FIG. 2 and deposited in *E. coli* HB101 under ATCC No. 39939.

The central portion of the MuLV pol gene of the plasmid may comprise the nucleotide sequence from about nucleotide 2574 to about nucleotide 4588. In one embodiment the 5' end of the central portion of the pol gene is 21 nucleotides from the start of the DNA sequence which encodes the polypeptide having reverse transcriptase activity.

Methods used in preparing the DNA vector and transforming suitable cells to the production of the polypeptide having reverse transcriptase activity are known in the art and described more fully hereinafter under Experimental Details.

Conventional cloning vehicles such as plasmids, e.g., pBR322, can be modified or engineered using known methods so as to produce novel cloning vehicles which contain DNA encoding a non-naturally occurring polypeptide having reverse transcriptase activity. Similarly, such cloning vehicles can be modified or engineered so that they contain DNA sequences, i.e., inducible promoters (Trp promoter, etc.), involved in the regulation or expression of the sequences encoding a polypeptide having reverse transcriptase activity. The DNA molecules so inserted may be made by various methods including enzymatic or chemical synthesis.

The resulting cloning vehicles are chemical entities which do not occur in nature and may only be created by the modern technology commonly described as recombinant DNA technology. These cloning vehicles, including the plasmid of this invention, may be introduced into a suitable host cell, either procaryotic, e.g., bacterial (*E. coli* or *B. subtilis,* etc.) or eucaryotic, e.g., yeast, using techniques known to those skilled in the art, such as transformation, transfection and the like. The one embodiment of this invention is the *E. coli* HB101 strain containing the plasmid pB6B15.23 deposited under ATCC No. 39939. The cells into which the plasmid of this invention is introduced will thus contain DNA encoding a non-naturally occurring polypeptide having reverse transcriptase activity. Further, the expression of the DNA encoding the non-naturally occurring polypeptide will be under the control of the Trp promoter.

The resulting cells into which DNA encoding the non-naturally occurring polypeptide encoding reverse transcriptase activity and encoding the Trp promoter has been introduced may be grown under suitable conditions known to those skilled in the art so as to control and effect the expression of the genetic information encoded by the DNA and permitting the production of the polypeptide having reverse transcriptase activity and the recovery of the resulting polypeptide. Thus one embodiment of this invention concerns the polypeptide so prepared, e.g. the polypeptide having reverse transcriptase activity characterized by being encoded by the plasmid pB6B15.23.

A further embodiment concerns a method for recovering the polypeptide of this invention from most cells in which it has been produced. The method comprises disrupting the cells, recovering soluble material containing the reverse transcriptase polypeptide from the disrupted cells and separately recovering the reverse transcriptase polypeptide from the soluble material in purified form. In a specific embodiment the separate recovery of the reverse transcriptase polypeptide comprises chromatography on phosphocellulose followed by chromatography on polyribocytidylic acid-agarose.

Still another embodiment of this invention is a method for reverse transcription of an RNA molecule. The method comprises contacting the RNA molecule with the polypeptide of this invention under suitable reverse transcribing conditions so as to produce a DNA molecule which is complementary to the RNA molecule.

EXPERIMENTAL DETAILS

FIRST SERIES OF EXPERIMENTS

Material and Methods

Bacteria. *Eschericia coli* strain HB101 (rec A13⁻, hsdR⁻, hsdM⁻, lacYl, SupE44) was used as the host for most experiments (11). The DNA Polymerase I-deficient strain C2110 (his-, rha-, polA1-) used to eliminate the presence of endogenous DNA synthetic activity, was the kind gift of D. Figurski. Cells were transformed to ampicillin resistance as described.

Plasmids. The trpE fusion vector pATH1, containing the 5' proximal part of the trpE gene followed by a polylinker sequence, was the generous gifts of T. J. Koerner and A. Tsagaloff. Plasmid pT11, containing a full-length copy of the M-MuLV genome was the source of the pol gene.

Enzymatic reactions. DNAs were digested with selected restriction enzymes (New England Biolabs) under conditions specified by the manufacturer. DNA fragments were purified by agarose gel electrophoresis and eluted by the glass powder method. DNA was treated with the enzymes exonuclease Bal31, nuclease S1, and T4 DNA ligase as described previously. Reverse transcriptase assays measured the incorporation of radioactive dTTP into homopolymer on synthetic templates as previously described. Product DNA was detected by measuring the radioactivity binding to DEAE paper (DE81; Whatman) by autoradiography or by scintillation counting in Aquasol (NEN).

DNA sequencing. The bases in plasmid pSHNB6 flanking the site of deletion were determined by the procedure of Maxam and Gilbert (9). Plasmid DNA was cleaved with Hinc II, and the 5' ends of the fragments were labelled with polynucleotide kinase. The 240-bp fragment containing the site of fusion was purified, the label at one end was removed by cleavage with Rsa I, and the DNA was subjected to chemical degradation and gel electrophoresis.

Preparation of crude lysates. These procedures were modifications of the method of Kleid et al. (12). Cultures (0.5 ml) were grown to stationary phase in M9 medium (13) plus 0.5% casamino acids, thiamine (10 $\mu$g/ml), tryptophan (20 $\mu$g/ml) and ampicillin (50 $\mu$g/ml), diluted 1:10 into medium without tryptophan, and grown for 1 h at 30° C. The cells were induced by addition of indoleacrylic acid to 5 $\mu$g/ml, grown an additional 2 h, and harvested by centrifugation. Total cell protein for gel analysis was isolated by resuspending the cells from 1 ml of culture in 50 $\mu$l of cracking buffer (6 M urea, 1% SDS, 1% SDS, 1% betamercaptoethanol, 10 mM sodium phosphate pH 7.2) at 37° C. for 1 h. Preparation of total protein extracts for enzymatic assays, and the subsequent separation of proteins into soluble and insoluble fractions were carried out as described (12). Extracts made by the dilute lysis procedure were prepared from small cultures lysed in 1/10th volume, and large-scale extracts made by the concentrated lysis procedure were made from 500 ml cultures lysed in 1/200th volume.

Immunoprecipitations. Cells (7.5 ml cultures) were labelled by addition of $^{35}$S-methionine to 40 $\mu$Ci/ml at the time of induction, treated with lysozyme as above, and lysed with PLB buffer (1% Triton X100, 0.5% sodium deoxycholate, 0.1% SDS, 10 mM sodium phosphate pH 7.5, and 0.1 M NaCl) for 15 min. at 0° C. After addition of fixed *S. aureus* cells (25 $\mu$l of a 1:1 suspension; Pansorbin, CalBiochem) the lysate was clarified (45,000 rpm, 90 min.), and 200 μl aliquots were incubated with antiserum (5 μl) overnight. The immune complexes were adsorbed to fixed *S. aureus* for 1 h at 0° C., collected and analyzed by SDS polyacrylamide gel electrophoresis as described (14).

Partial purification of pSH1 and pSHNB6 proteins. HB101 cells bearing pSH1 or pSHNB6 were grown to stationary phase at 37° C. and induced as above. The cells were collected by centrifugation, washed, resuspended in 1/200th volume of buffer (50 mM Tris-Cl pH 7.5, 0.5 mM EDTA, 0.3 M NaCl), and treated with lysozyme (1 mg/ml) at 0° C. for 30 min. The cells were lysed with NP40 (0.2%), and the lysate was made 1 M in NaCl, clarified at 8000 xg for 30 min., and dialyzed against buffer B (50 mM Tris-Cl ph 8.0, 1 mM EDTA, 1 mM dithiothreitol, 10% glycerol) containing 0.1% NP40 and 25 mM NaCl. DNA was precipitated by the addition of 0.3 volumes of streptomycin sulfate solution (5% in buffer B containing 25 mM NaCl), and the supernatant was applied to a DEAE cellulose column (DE52; Whatman) equilibrated with buffer B plus 25 mM NaCl. The activity was eluted with buffer B plus 0.2 M NaCl.

Ammonium sulfate fractionations. Activity eluted from DEAE cellulose columns was precipitated by the addition of solid ammonium sulfate to the appropriate concentration. The solution was stirred for 1 h, and the precipitate was pelleted (11,000 rpm, 30 min.).

RESULTS

Figure 1:
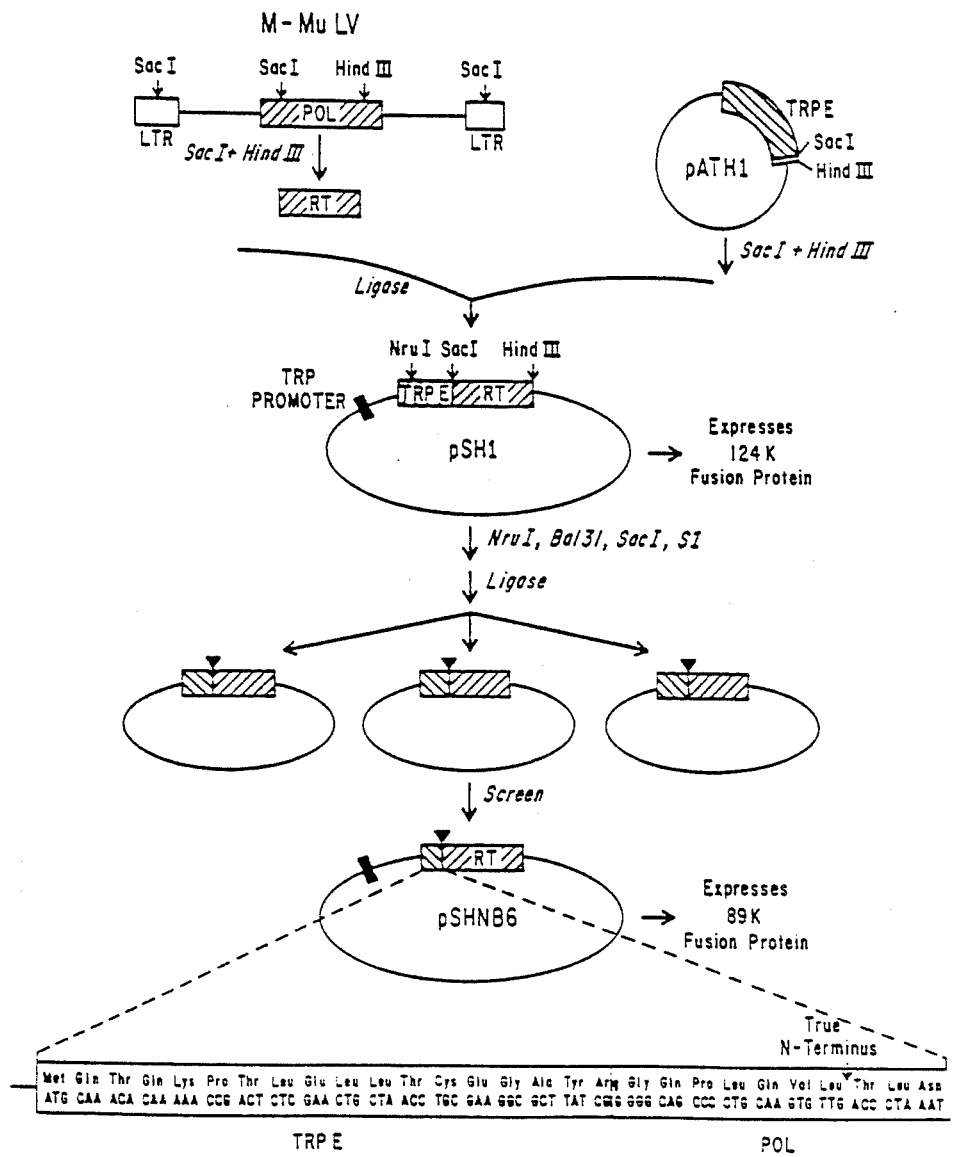
FIG. 1. Construction of trpE-pol gene fusions. The central portion of the pol gene was excised from a cloned copy of the M-MuLV genome by cleavage with Sac I plus Hind III and inserted into the polylinker sequence of the expression vector pATH1. The resulting plasmid, pSH1, expressed a 124,000 dalton fusion protein and substantial levels of active reverse transcriptase. In a second step, the bulk of the trpE sequences and varying amounts of the pol gene were deleted, and bacterial clones were screened for increased levels of reverse transcriptase activity. The highest-level producer, pSHNB6, encoded an 89,000-dalton protein. The DNA sequence in the region of the deletion, along with the predicted amino acid sequence of the encoded protein, is indicated.

Construction of TrpE-pol gene fusion. In our initial effort to express reverse transcriptase, we chose a fragment from the central portion of pol gene of the biologically active copy of the viral genome cloned in the plasmid pT11 (15). Sac I cleaves within the 5' portion of the pol gene encoding the viral protease; a deletion mutation near this site does not effect reverse transcriptase activity (16). Similarly, Hind III makes a single cleavage in the 3' portion of the pol gene; deletions at this site also did not affect production of the enzyme (17). The 2.5 kb fragment produced by cleavage with Sac I plus Hind III was isolated and inserted into the polylinker sequence of the expression vector pATH1 (T. J. Koerner and A. Tzagoloff, Personal Communication.) The resulting plasmid, pSH1, contained the TrpE promoter, 326 codons of the trpE gene, and the coding region for the central portion of trpE the pol gene appended in the correct reading frame (FIG. 1). The gene product would contain 36,200 daltons of the trpE polypeptide joined to 87,7000 daltons of pol protein; translational termination of the fusion protein would occur at an amber codon immediately downstream of the pol sequences.

In an attempt to form smaller protein products that would more closely resemble the authentic enzyme, we modified the initial construct. We removed the bulk of the trpE sequences and portions of the 5' end of the pol gene by creating a series of deletion mutations in the pSH1 plasmid. The general scheme used to create the deletions is shown in FIG. 1. pSH1 DNA was cleaved near the 5' end of the trpE gene with Nru I, and treated with the exonuclease Bal31; the DNA was recleaved with Sac I at the 3' end of the trpE gene, and the termini were blunted with nuclease S1. The linear DNA was purified, recyclized with T4 DNA ligase, and used to transform HB101 cells to ampicillin resistance. Two-thirds of these clones should contain frameshift mutations; only one-third might encode improved levels of activity. Approximately 100 clones were recovered from this procedure. Analysis of the DNA from several colonies showed that varying amounts of the trpE and pol genes had indeed been removed (data not shown).

The TrpE-pol fusions induce reverse transcriptase activity. Cells containing pATH1 and pSH1 were starved for tryptophan, harvested, and lysed, and the crude extracts were tested for reverse transcriptase activity. The assay measured the incorporation of radioactive dTTP on a synthetic template (polyriboadenylate) primed with oligo dT and was similar to identical assays previously used to detect the viral enzyme (18). Extracts prepared from HB101 cells, or from cells bearing pATH1, showed significant basal activity in the assay. The bulk of this background activity is attributable to the presence of DNA polymerase I in the extracts; this enzyme is known to exhibit reverse transcriptase activity (19). Cells bearing plasmid pSH1 consistently showed four to six fold higher activity over the control cells (Table 1). The level of activity per ml in these crude extracts was considerably higher than that in viral harvests taken from infected NIH/3T3 cell lines. Recovery of the activity in the soluble fraction required the presence of nonionic detergent and high salt concentrations (data not shown).

TABLE 1

DNA synthesis on synthetic templates by bacterial extracts; sensitivity to NEM.

| | Cells | Plasmid | Treatment | pmol incorporated per μl |
|---|---|---|---|---|
| Expt 1: | HB101 | pATH1 | lysate | 2.00 |
| | HB101 | pATH1 | +NEM, then DTT | 1.55 |
| | HB101 | pATH1 | +DTT, then NEM | 1.40 |
| | HB101 | pSH1 | lysate | 23.7 |
| | HB101 | pSH1 | +NEM, then DTT | 2.48 |
| | HB101 | pSH1 | +DTT, then NEM | 15.9 |
| | HB101 | pSH1 | +premixed DTT+NEM | 16.9 |
| Expt 2: | HB101 | pATH | lysate | 59.6 |
| | HB101 | pATH1 | +NEM, then DTT | 45.7 |
| | HB101 | pSH1 | lysate | 751 |
| | HB101 | pSH1 | +NEM, then DTT | 98.2 |
| | HB101 | pSHNB6 | lysate | 2090 |
| | HB101 | pSHNB6 | +NEM, then DTT | 237 |
| | C2110 | pSH1 | lysate | 1590 |
| | C2110 | pSH1 | +NEM, then DTT | 164 |
| Expt 3: | HB101 | pSH1 | DEAE eluate | 112 |
| | HB101 | pSH1 | +NEM, then DTT | 27.3 |
| | HB101 | pSH1 | 40-70% AS fraction | 140 |
| | HB101 | pSH1 | +NEM, then DTT | 94.4 |
| | HB101 | pSH1 | 0-40% AS fraction+ | 252.6 |
| | HB101 | pSH1 | NEM, then DTT | 25.5 |

Lysates were prepared from the indicated bacterial Cells carrying the indicated plasmids, and assayed for reverse transcriptase after various treatments. Entries are the pmoles of $^{32}$p-dTTP incorporated into DNA per microliter of extract under standard conditions (see Methods). Extracts for expt.1 were made by the dilute lysis procedure, those for expt. 2 by the concentrated lysis procedure, and those for expt 3. as in the text. Protein concentrations (mg/ml) were: expt. 1: 1. 34 and 1.51; expt. 2: 3.82, 3.10, 3.53, and 3.6; expt. 3: 1.05, 2.39, and 0.59.

To test whether the increased activity could be attributed to an increase in the level of DNA polymerase I, the sensitivity of the activity to the sulfhydryl reagent N-ethyl maleimide (NEM) was determined. The authentic murine reverse transcriptase is exquisitely sensitive to the sulfhydryl reagent N-etheyl maleimide (NEM), while the bactefial DNA polymerase I is resistant (20). Treatment of the extracts of HB101, or of HB101 carrying pATH1, with NEM had no effect on the activity; but treatment of extracts of cells carrying pSH1 reduced the high level of activity to that of the control extracts. This result suggested that the pSH1 plasmid induced a novel reverse transcriptase activity with properties similar to those of the authentic enzyme.

Further evidence that the additional activity was not due to elevated levels of DNA polymerase I was obtained by repeating the assays in a bacterial host carrying a mutation in polA, the structural gene for the enzyme. Strain C2110 (polA1-) was transformed to ampicillin resistance with the plasmids pATH1 and pSH1; because the gene is required for plasmid replication, these transformations occur at low frequency. The plasmids are apparently maintained by recombination with the host chromosome. The continued presence of the polA1- mutation was confirmed (21) by testing the strains for sensitivity to methylmethane sulphonate (MMS). Extracts of strain C2110, or of strain C2110 bearing the pATH1 vector, showed no measurable reverse transcriptase activity in the assay, confirming that the background activity of HB101 was indeed due to DNA polymerase I. Reverse transcriptase assays of bacterial extracts of total proteins were performed. Aliquots were incubated in a reaction cocktail containing labelled precursors, and the products were spotted on DEAE paper, washed, and exposed to X-ray film. The extracts of HB101 cells carrying the indicated plasmid were prepared and either 0.1 microliters, 1 microliter, or 10 microliters were assayed. Cells carrying pSH1 expressed nearly a 10-fold higher level of activity over control cells. Virus preparation from infected NIH/3T3 cells (10 microliters) was also performed. HB101 cells carrying the indicated plasmids were assayed using 1 microliter or 5 microliters of extract. C2110 cells carrying the indicated plasmids were assayed as before. Extracts of C2110 bearing pSH1 showed the same high levels of activity seen in the HB101 host. Reverse transcriptase assays as a screen of cloned variants of the pSH1 plasmid. Amounts of 0.1 ul total protein extract from each clone were assayed as described below. Cells carrying pATH-1 and pSH1 were used as standards. One plasmid, pSHNB6, showed significantly higher levels than the parent. Plasmid pSHNB63 showed a high level comparable to that of pSHNB6. Although some constructs showed higher levels than pSH1, none equalled the levels of pSHNB6 and pSHNB63. These results suggest that the plasmid specified considerable reverse transcriptase activity, independent of DNA polymerase I. It is noteworthy that the single copy of the gene fusion in the C2110 cells expressed as much activity as the multicopy genes in HB101.

Removal of the trpE sequences results in increased enzyme activity.

Cultures containing each of the variant plasmids generated by mutagenesis of pSH1 were grown and starved for tryptophan; extracts were assayed for reverse transcriptase activity as before. Approximately 100 independent clones were screened, and two were found to produce dramatically higher levels of activity than the parental pSH1 plasmid. One of these clones, carrying plasmid pSHNB6, was chosen for further study. Quantitative assays reproducibly showed that cells carrying the new plasmid expressed a 4–8 fold higher level of activity than cells carrying pSH1; the cells showed as much as a 35-fold increase in activity over cells carrying the pATH-1 vector alone (Table 1).

Restriction analysis of the pSHNB6 DNA showed that the bulk of the trpE sequences had been successfully removed, and that only a short part of the 5' end of the trpE gene was joined to the pol sequences. To define the precise junction in this clone, the DNA sequence of this region was determined by the procedure of Maxam and Gilbert (9). The sequence (FIG. 1) showed that 18 codons of trpE were joined, in the correct reading frame, to the pol gene; 17 bp had been removed from the pol gene by the S1 treatment, leaving only 7 codons of pol sequence 5' to the start of the mature reverse transcriptase. This deletion in this active clone did not extend upstream of the Nru I site, in contrast to the deletions present in many less active clones. The plasmid in the second highly active clone, pSHNB63, also retained similar trpE coding sequences (data not shown). These results suggest that the presence of the trpE codons upstream of this site may help to stabilize the protein product.

Analysis of fusion proteins encoded by pSH1 and pSHNB6.

We next analyzed the polypeptides synthesized in HB101 cells carrying the pSH1 and pSHNB6 plasmids. Both the total proteins, and the proteins remaining insoluble after addition of detergent and high salt concentrations were isolated (12). These fractions were subjected to SDS polyacrylamide gel electrophoresis, and the proteins were detected by Coomassie stain. Cells transformed with the pATH1 vector alone contained large amounts of a truncated trpE protein migrating at the position of a 37,000-dalton polypeptide; as previously reported, the majority of this protein was recovered in the insoluble fraction (22). The sequence of the pSH1 plasmid predicted the formation of a fusion protein containing both the trpE and pol polypeptides, of 124,000 daltons; cells carrying pSH1 exhibited a major new protein migrating at approximately 120,000 daltons, in good agreement with the expected size. Virtually all of this polypeptide was recovered in the insoluble fraction. In addition, many smaller proteins specific to cells carrying pSH1 were detected. These proteins, ranging in size from 110,000 to 52,000 daltons, represented a major portion of the total mass of the new protein induced by pSH1. We have found that extended formation of these smaller proteins, and that the addition of protease inhibitors during the lysis did not reduce the formation of these products.

The structure of the pSHNB6 plasmid predicted the synthesis of a protein of 89,000 daltons; examination of cells carrying pSHNB6 showed substantial amounts of a new protein of about 90,000 daltons, as well as lesser amounts of smaller proteins. SDS polyacrylamide gel electrophoresis of bacterial proteins from HB101 cells carrying various plasmids was performed. Proteins were analyzed by Coomassie blue staining. Experiments were performed on proteins of HB101 cells containing vector pATH1 alone; total proteins of HB101 cells containing plasmid pSH1; insoluble fraction from cells carrying pATH; and insoluble fraction from cells carrying pSH1. Coomassie staining of insoluble proteins was performed on gels containing (a) cells without plasmid, (b) cells carrying pSHNB6. A fluorogram of proteins metabolically labelled after induction of the trp operon in cells carrying pSHNB6 was also performed. The major bands induced by pSHNB6 are visible at 90, 70, and 60 kilodaltons. Immunoprecipitation of bacterial proteins was performed. Cultures were labelled with 35S-methionine after induction of the trp operon, and the soluble proteins extracted with detergents (see Methods). The extracts were incubated with various sera, and the immune complexes were collected with S.

*aureus cells.* The bound proteins were analyzed by SDS gel electrophoresis and fluorography. The gels contained samples of proteins of control HB101 cells carrying the vector pATH1; proteins of HB101 cells carrying pSH1; proteins of HB101 cells carrying pSHNB6; normal rabbit serum; rabbit serum specific for the trpE protein; NCI serum #775-424 specific for reverse transcriptase; and NCI serum #775-454 specific for reverse transcriptase. These proteins could be detected in total lysates, but there were high levels of other bacterial proteins in the same region of the gels. Analysis of the proteins labelled with 35S-methionine at the time of induction of the trpE gene clearly revealed the 90,000 dalton protein and two major species at approximately 70,000 and 60,000 daltons.

The identity of these proteins as products of the gene fusion was confirmed by immunoprecipitation with specific antisera. Cells were labelled with 35S-methionine after induction of the trp operon. The proteins were extracted with strong detergents, immunoprecipitated with specific sera, and analyzed by electrophoresis and fluorography. All cells tested showed high levels of a 60 kd protein which was nonspecifically precipitated by all sera; cells carrying pATH1 contained in addition high levels of trpE proteins in the range of 30 to 35 kd which were specifically precipitated by serum prepared against the trpE polyprotein. These control cells contained no proteins reactive with sera raised against authentic murine reverse transcriptase.

Cells carrying pSH1 contained new proteins reactive with the specific sera. A protein of 120,000 daltons, and a number of smaller polypeptides ranging in size from 110,000 to 60,000 daltons were barely detectable with the trpE serum. A similar spectrum of proteins was readily seen with either of two sera reactive with reverse transcriptase (lanes 7 and 8), demonstrating that the new proteins contain determinants of both trpE and reverse transcriptase. The soluble fractions were highly enriched for the smaller proteins relative to the full-length product, compared with the insoluble fraction, suggesting that the small proteins were selectively extracted.

Immunoprecipitation of the proteins from cells carrying pSHNB6 with sera specific for viral reverse transcriptase showed that a 90,000 dalton protein and at least one major smaller protein were also recognized by the sera. A higher proportion of the full-size pSHNB6 protein was recovered in the soluble fraction than with the corresponding pSH1 protein. Thus, the removal of the bulk of the trpE sequences, and possibly part of the 5'-pol sequences, resulted in the synthesis of a smaller protein with increased solubility, improved stability to proteolytic degradation, and exhibiting a higher level of reverse transcriptase activity. We have not determined whether the higher activity is due solely to an increase in the amount of soluble full-size protein recovered, or whether it is due in addition to an increase in the specific activity of the enzyme.

Partial purification of the pSHNB6 protein

To characterize the new activities induced by the gene fusions, and to demonstrate that the DNA synthetic activity was not due to DNA Polymerase I, we partially purified the activities. Large-scale cell cultures were prepared and starved for tryptophan as before. The cells were harvested, washed, and lysed by treatment with lysozyme and NP40 detergent, and the insoluble material removed by centrifugation (see Methods). The salt concentration was reduced by dialysis, and the bulk of the DNA in the solution removed by precipitation with streptomycin sulphate; 80% of the activity remained soluble through this procedure. The material was applied to a DEAE cellulose column at a low ionic strength, and the activity was recovered by elution with buffer containing 0.2 M NaCl.

Fractionation of the eluate from cells carrying pSH1 by ammonium sulfate precipitation showed (Table 1) that most of the activity was recovered in the fraction precipitated by 40% saturated ammonium sulfate. The proportion of the activity that was sensitive to NEM was monitored as before. The bulk (90%) of the activity in this fraction was sensitive to NEM, indicating that the activity was due to the pSH1 enzyme. The rest of the initial activity was recovered in the 40-to-70% ammonium sulfate fraction, known to contain DNA polymerase I (23). This activity, as expected, was largely resistant to NEM treatment.

The activity induced by pSHNB6 behaved similarly. After elution from DEAE cellulose, the bulk of this activity was precipitated by addition of ammonium sulfate to 45% of saturation, and the fraction of the activity which was sensitive to NEM was monitored as before. The crude material was 23% resistant. The activity which was precipitated by ammonium sulfate was only 9.5% resistant, and was therefore enriched for reverse transcriptase-like activity; the activity which remained soluble was now 72% resistant, and therefore consisted largely of DNA polymerase I. Further purification of the pSHNB6 protein on phosphocellulose showed that the activity could be bound and eluted with buffer containing 0.1–0.2 M NaCl. Preliminary characterization of this activity showed that long DNA products could be synthesized, and that RNAse H activity had copurified through these steps. A more detailed description of the purification and characterization of this and similar fusion proteins will follow.

Discussion

These experiments demonstrate that portions of the pol gene of a mammalian retrovirus can be expressed as a gene fusion with the bacterial trpE gene. The fusion proteins are sufficiently abundant and stable to be detected after electrophoresis of the total bacterial proteins, and are major proteins in an insoluble fraction of the lysate. Our crude estimate is that the pol-related products represent about 1% of the total protein after induction of the trp operon. Extracts containing these proteins show reverse transcriptase activity, as assayed by the synthesis of DNA on ribohomopolymer templates. The level of activity is many-fold greater than the low activity due to the endogenous DNA polymerase I, is independent of the polA gene in the host, and shows biochemical properties distinct from those of this enzyme.

It is clear that the gene constructs lead to the formation of shorter products as well, probably formed by degradation of the primary translation product within the cell. The shorter products may be responsible for much of the detectable activity. Thus, many modifications in the gene fusion which allow the direct formation of similar, smaller proteins might yield higher levels of recoverable activity. The increased activity seen for the SHNB6 construct is consistent with this notion. Recently, further efforts to trim the size of the gene to its minimum have recently led to the synthesis of products with increased solubility, stability, and activity.

We believe that the expression of the murine reverse transcriptase in bacterial cells will lead to several important projects. Firstly, the availability of large quantities of the purified enzyme will allow extensive characterization of the enzyme. Secondly, mutations can be readily introduced into the cloned gene fusions, and large numbers of bacterial cultures can be screened for the presence of rare variants exhibiting desirable changes in the activity. It may be possible, for example, to construct variants which do not express RNAse H activity. Thirdly, mutations such as temperature-sensitive mutations can also be generated, and a DNA fragment containing the alteration can be recovered and reinserted into the complete viral genome. In this way it may be possible to study the effects of many new mutations on the retroviral life cycle and determine new functions for the reverse transcriptase enzyme.

SECOND SERIES OF EXPERIMENTS

Materials and Enzymes ($\alpha^{32}$P) dATP, ($\alpha^{32}$P) TTP, and ($\alpha^{32}$P) dCTP were purchased from Amersham; ($^3$H) ATP and ($\alpha^{32}$P) ATP were from ICN. DEAE-cellulose (DE52), phosphocellulose (P11), and DEAE-cellulose paper (DE81) were obtained from Whatman. Agarose-polycytidilic acid was either purchased from PL Biochemicals or synthesized as described (24). Polycytidilic acid was purchased from PL Biochemicals. Cyanogen bromide activated agarose, 3-indoleacrylic acid, and protein molecular weight standards were purchased from Sigma, lysozyme from Worthington, and p-Toluenesulfonylflouride from Kodak. E. coli RNA polymerase was purified as previously described (25,26). Bal 31 nuclease was purchased from IBI; T4 Polynucleotide Kinase from BRL; Calf Intestinal Alkaline Phosphatase from Boehringer Mannheim; and all restriction endonucleases from New England Biolabs. T4 DNA ligase was a gift of J. van Oostrum, of this department. PolyA+ RNA from human fetal muscle tissue was a gift of L. Saez, Albert Einstein College of Medicine, Bronx, N.Y. Total RNA from human reticulocyte lysate was a gift of Dr. C. Dobkin, this institution. Actinomycin D was a gift of Dr. S. Silverstein, this institution. Sera specific for the N-terminal 37,000 daltons of the TrpE protein was a gift of Dr. O. Witte, University of California, Los Angeles. Sera #775-424 and #775-454 were raised in goat against Rauscher reverse transcriptase and obtained from the National Institutes of Health. The Rauscher reverse transcriptase was isolated by ion exchange chromatography and gradient centrifugation. The sera showed cross reactivity to the reverse transcriptase and P30$^{gag}$ proteins.

Buffers

Hind III and Pvu I digestion buffer contained 10 mM Tris-HCl buffer, pH 7.5, 6 mM MgCl$_2$, 0.1 mM dithiothreitol, and 60 or 120 mM NaCl, respectively. Buffer M contained 50 mM Tris-HCl buffer, pH 7.0, 1 mM EDTA, 1 mM dithiothreitol, 0.1% nonidet P40, and 10% glycerol. Storage buffer contained 50 mM Tris-HCl buffer, pH 8.0, 1 mM EDTA, 5 mM dithiothreitol, 0.1% nonidet P40, 0.1 M NaCl, and 50% glycerol.

GROWTH OF BACTERIA

A liter of HB101 cells containing plasmid pB6B15.23 was grown overnight at 37° C. in supplemented media (see above) in the presence of tryptophan. The cells were diluted twelve fold in supplemented media lacking tryptophan, and grown at 30° C. until the culture reached an O.D.$_{600}$ of 0.5. Indoleacrylic acid was then added to a concentration of 5 μg/ml, and growth was continued to a final O.D.$_{600}$ of 0.8-1.0. Cells were collected in a Sharpel centrifuge, washed in 50 mM Tris-HCl buffer, pH 7.5, 0.5 mM EDTA, and 0.15 M NaCl, spun at 3300 xg for 20 minutes, resuspended (1:1 w/v) in 50 mM Tris-HCl buffer, pH 7.5, and 10% sucrose, and frozen in an ethanol/dry ice bath.

Reverse Transcriptase Assay

RNA-dependent DNA polymerase activity was assayed as previously described (18) with the following modifications: (1) assays (50 μl) contained 10 μg/ml oligo dT and 20 μg/ml poly rA; (2) incubations were at 37° C. for 15 minutes; (3) 40 μl aliquots were removed, spotted on DE81 chromatography paper, and washed three times in 0.3 M NaCl, 0.03 M NaCitrate (2X SSC) for 5 minutes each. Filters were washed in ethanol and the radioactivity was determined by liquid scintillation counting in Aquasol aqueous scintillant.

Preparation of DNA-($^3$H)RNA hybrid

Reaction mixture (500 μl) contained 40 mM Tris-HCl buffer, pH 7.9, 32 nmol of M13 single stranded circular DNA, 8 mM MgCl$_2$, 2 mM dithiothreitol, 100 mM KCl, CTP, GTP, and UTP each at 115 μM, 55 μM of ($^3$H) ATP (specific activity=1142 cpm/pmol), and 28 μg of E. coli RNA polymerase. The mixture was incubated at 37° C. for 75 minutes, the reaction was stopped by the addition of 10 mM EDTA, and the products were extracted with an equal volume of phenol, ether extracted twice, and concentrated by vacuum centrifugation. The fraction (50 μl) was loaded onto a G-50 column (1×22 cm). The $^{32}$p-labeled material which eluted in the void volume was pooled, concentrated by vacuum centrifugation, and precipitated with 2.5 volumes of ethanol in the presence of 1 M ammonium acetate. The pellet was washed with 70% ethanol, and resuspended in 5 mM Tris-HCl buffer, pH 7.5, 0.5 mM EDTA (1 ml).

RNase H assay

Reaction mixtures (50 μl) contained 40 mM tris-HCl buffer, pH 8.0, 2 mM dithiothreitol, 40 mM KCl, 1 mM MnCl$_2$, and 10 pmol of ($^3$H) AMP incorporated into DNA-($^3$H)RNA hybrid and enzyme as indicated. Mixtures were incubated for 30 minutes at 37° C., and the reactions were stopped by the addition of NaPP$_1$, pH 6.0, to final concentration of 0.05 M (50 μl) and 250 μg sonicated salmon sperm DNA. Precipitation of the residual RNA/DNA was carried out in the presence of 20 μg bovine serum albumin by the addition of trichloroacetic acid to 8%. The mixture was kept on ice for 10 minutes and spun for 10 minutes in an Eppendorf microcentrifuge, and an 150 μl aliquot of the supernatant was counted for ($^3$H) radioactivity using Aquasol liquid scintillant.

Protein determination

Protein concentration was determined using the method described by Bradford (27).

Isolation of polyA+RNA

Oligo(dT)-celluose column chromatography was performed as described (28). 340 μg of total RNA from human reticulocyte lysate was loaded onto a column (200 μl) and the bound fraction was collected (1.2 ml), precipitated in ethanol in the presence of 0.4 M NaCl, washed three times in 70% ethanol and once in 100% ethanol. The pellet was resuspended in 14 μl of 10 mM Tris-HCI buffer, pH 7.5 and 1 mM EDTA.

Enzymatic manipulations of DNA 11.5 μg of pSHNB6 plasmid prepared as described (29) was linearized with Hind III restriction enzyme (40 units) as described above. The reaction mixture was incubated for 2 hours at 37° C., extracted with an equal volume of phenol two times, ether extracted twice, and precipitated with 2.5 volumes of ethanol in the presence of 0.5 M NaCl Pellets were dried under vacuum and resuspended in 600 μl of Bal 31 buffer (20 mM TrisHCl, pH 8.0, 600 mM NaCl, 12.5 $CaCl_2$ and 12.5 MM $MgCl_2$). To each of six 100 μl aliquots, 1.8 units of Bal 31 exonuclease (IBI) was added and the mixtures were incubated at 30° C. for either 0, 7.5, 15, 30, 45, or 60 minutes. Digestion was terminated by addition of sodium dodecyl sulfate and EDTA to a final concentration of 0.1% and 12 mM, respectively. Reaction mixtures were heated at 65° C. for 15 minutes, phenol extracted, ether extracted, and precipitated in ethanol as described above. The pellet was resuspended in PvuI buffer and digested with 8 units of Pvu I restriction enzyme. The reaction was quenched with electrophoresis sample buffer (10% glycerol, 0.1% sodium dodecyl sulfate, 20 mM EDTA) and the DNA was fractionated by electrophoresis in a 0.8% agarose gel containing 1 μg/ml ethidium bromide in TEA buffer (50 mM Tris-HCl, 1 mM EDTA, Acetic acid to pH 8.0). Inspection of the DNA under UV light indicated that the rate of digestion was 30 bases/minute and that the Pvu I digestion was not to completion. The predominant DNA species for each time point was isolated form the gel by the glass powder method (30). In parallel, the parent plasmid pATH1, was in digested with SmaI (20 units) in buffer (6 mM Tris-HCl buffer, pH 8.0), 20 mM KCL, 6 mM $MgCl_2$, 1 mM dithiothreitol, and 100 μg/ml bovine serum albumin for 2 hours at 37° C. and subsequently with Pvu I (8 units) after the addition of 100 mM NaCl. The 780 base fragment was isolated from a 1.2% agarose gel as described above. The 780 base fragment isolated from pATH1 and the approximately 5000 base long fragment isolated after Bal 31 digestion of pSHNB6 for either 7.5 or 15 minutes were mixed and treated as described (20) with 3.5 μg of T4 DNA ligase at 15° C., overnight Since the Pvu I digestion on pSHNB6 was to completion, two constructs could be formed. One would result from an intramolecular ligation of linear molecule which was bidirectionally digested with Bal 31 nuclease. The termination codon for the protein would appear randomly within the plasmid sequence depending on the extent of the nuclease digestion. Alternatively, intermolecular joining of the two fragments could result in a unidirectional deletion. This would result in a known DNA sequence and defined terminator codons being placed 3' downstream of the coding region of the gene. Aliquots of the ligation reaction mixtures were used to transform E. coli HB101 to ampicillan resistance (31). Plasmids isolated from colonies (32) were screened for deletions using Sal I, PvuII, Bgl I, Bgl II, and XmnI. Although two possible constructs could have been made, only the intermolecular ligation described above was detected.

Screening deletion mutants for Reverse Transcriptase Activity

Crude extracts of colonies were made as described (see Bacterial strains and media) and assayed for reverse transcriptase activity, with the following modifications: (1) Two hours after induction with indoleacrylic acid, a 5 ml culture was spun in a Savant Speedvac concentrator in the absence of a vacuum. The pellet was washed in 1.25 ml of 50 mM Tris-HCl buffer, pH 7.5, 0.5 mM EDTA, and 0.15 M NaCl, transferred to 1.5 ml microfuge tubes and recentrifuged. (2) The time of lysozyme digestion and nonidet P40 treatment was increased to 30 and 15 minutes, respectively. (3) The soluble extract was assayed for activity.

Immune Precipitation

Extracts for immune precipitation were prepared as described for screening of deletion mutants (see above) with the following modifications. ($^{35}$S)-methionine was added to 40 μCi/ml (7.5 ml culture) at the time of indoleacrylic acid addition. Uninduced control cultures of pB6B15.23 were grown in the presence of supplemented M9 media plus (50 μg/ml) ampicillin and 200 mg/ml tryptophan throughout; indoleacrylic acid was omitted. Cells lacking plasmids were grown in the absence of ampicillin. After digestion with lysozyme, the solution was made 1% Triton X100, 0.5% sodium deoxycholate, 0.1% sodium dodecyl sulfate, 10 mM NaPi, pH 7.5, and 0.1 M NaCl (1X phospholysis buffer). The mixture was kept on ice for 15 minutes and 1.13 ml of 1X phospholysis buffer and 25 ul of formalin-fixed, heat-killed cells Staphylococcus aureaus cells (Pansorbin resuspended 1:1 v/v in phospholysis buffer plus 1% bovine serum albumin) were added. The mixture was spun in a Ti50 rotor at 45,000 rpm for 90 minutes, and 200 μl aliquots of the supernatant were incubated with each antibody (5 μl) overnight. The complexes were absorbed to Pansorbin for 1 hour on ice, and collected by centrifugation Pellets were washed twice in 500 ul of 1X phospholysis buffer and resuspended in 0.125 M Tris-HCl buffer, pH 6.8, 2% sodium dodecyl sulfate, 20% glycerol, 0.01% bromophenol blue, 62 mM EDTA, and 2% mercaptoethanol (50 μl). Samples were boiled for 10 minutes and aliquots (30 μl) were subjected to sodium dodecyl sulfate polyacrylamide gel electrophoresis (10% polyacrylamide separating gel, 6% polyacrylamide stacking gel). The gel was washed 3 times for 5 minutes in $H_2O$, and once in 1 M sodium salicylate for 30 minutes, dried and subjected to autoradiography.

ATPase Assay

Reaction mixtures (25 μl) contained 50 mM Tris-HCl, pH 8.3, 2 mM DTT, 2 mM $MgCl_2$, and 1 mM ($\delta^{32}$P) ATP (2 cpm/pmol), and levels of enzyme varying between 29 and 145 units. The mixtures also contained either no DNA, φX174 single stranded circles (380 ng), phage lambda DNA digested with Hind III (750 ng), or a mixture of poly (rA) and oligo (dT) (1 and 0.5 μg, respectively). Reactions were incubated at 37° C. for 30 minutes, spotted on polyethyleneimine plates, chromatographed in 1 M $KH_2PO_4$, pH 3.4, and subjected to autoradiography.

Figure 3:
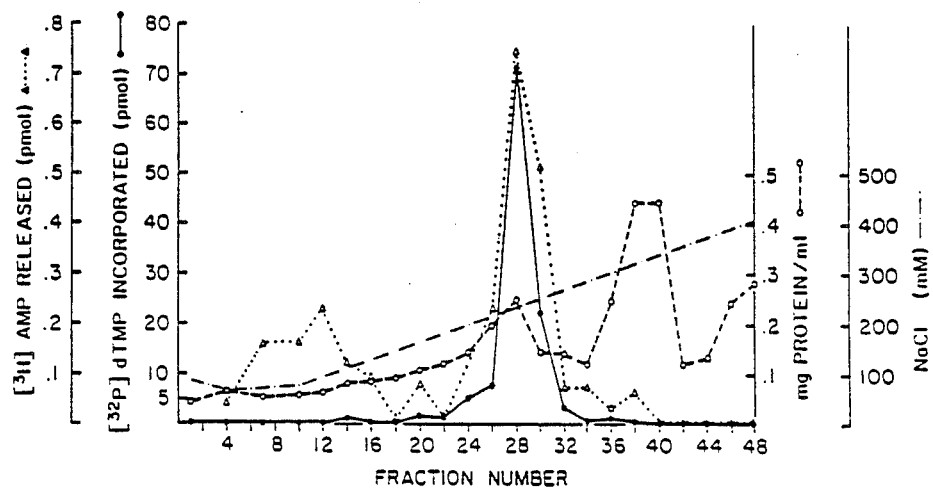
FIG. 3. Phosphocellulose chromatography The material which did not bind to DEAE-cellulose was chromatographed on phosphocellulose as described in the text. After collection of the material which did not absorb to phosphocellulose (not shown), the column was eluted with a gradient of NaCl as indicated. Aliquots of the individual fractions were diluted (1:100) in Buffer M plus 0.2 M NaCl, and 1 l of the dilution was assayed for reverse transcriptase activity (●—●) and RNase H activity (Δ—Δ) as described in the Experimental Procedures. 25 μl aliquot of the column eluant was assayed directly for total protein (O —O) as described in Experimental Procedures.

Purification of Reverse Transcriptase Activity 7 grams (packed cell weight) of HB101 cells containing pB6B15.23 induced as described above were thawed and made 50 mM Tris-HCl, pH 7.5, 10% sucrose, 0.3 M NaCl, 1 mM EDTA, and 1 mM PMSF to a final w/v ratio of 1:4. Lysozyme (1 mg/ml, final concentration) was added and the suspension was kept on ice for 10 minutes. Nonidet P40 was then added to a final concentration of 0.2%. The lysate was incubated an additional 5 minutes, was made 1 M with NaCl, and was centrifuged at 30,000 rpm in a Ti60 rotor for 30 minute. The supernatant was dialyzed for 1 hour against Buffer M, and then diluted with Buffer M to a conductivity equivalent to that of buffer M plus 75 mM NaCl (total volume=238 ml). The fraction was loaded on to a DEAE column (4×16.5 cm; DE52, Whatman equilibrated with Buffer M+75 mM NaCl. The column was washed with the same buffer. Most of the reverse transcriptase activity was not retained by the resin (see Table 2). The flow through fraction was applied directly onto a phosphocellulose column (2.5×28 cm; P-11, Whatman) equilibrated with Buffer M +75 mM NaCl. The column was washed with 1 column volume of the same buffer and eluted with 650 ml linear gradient of 75–700 mM NaCl in Buffer M. Fractions (10 ml) were collected and assayed for reverse transcriptase and RNase H activities. As shown in FIG. 3, the reverse transcriptase activity was completely retained on the column and eluted as a single peak between 0.21–0.24 M NaCl. The predominant RNase H activity was coincident with the reverse transcriptase activity. Phosphocellulose fractions 27–30 were pooled (42.5 ml). Aliquots (10 ml) were diluted in Buffer M to a conductivity equivalent to 50 mM NaCl in Buffer M and loaded individually onto an Agrarose-polyribocytidilic acid column (1.1×8.5 cm) equilibrated in Buffer M containing 50 mM NaCl. The column was washed with 1 column volume of the same buffer and eluted with a linear (56 ml) gradient of 50 to 300 mM NaCl in Buffer M. The reverse transcriptase activity, the RNase H activity, and the total protein co-chromatographed and eluted in a coincident peak between 135–180 mM NaCl. Fractions 24–34 were pooled and concentrated by hydroxylapatite column chromatography. The fraction was loaded on a column (1.3×3 cm) equilibrated in Buffer M containing 0.22 M NaCl, washed with 1 column volume of the same buffer, and eluted with Buffer M containing 0.2 M NaCl and 100 mM $NaP_i$, pH 7.0. Fractions (1ml) were collected; those containing reverse transcriptase activity were dialyzed for 7 hours against storage buffer and kept at −70° C. in aliquots.

RESULTS

Construction of a Gene Fusion Expressing Stable Fusion

An outline of the scheme used to stably express the MuLV reverse transcriptase activity is presented in FIG. 2. The initial construct used as the starting material for further manipulation was the plasmid pSHNB6, containing the region of M-MuLV from nucleotide position 2574 to 4893 (8) inserted in frame downstream of the first eighteen codons of the E. Coli trpE protein (6). Our earlier work demonstrated that extracts of E. coli strains bearing this plasmid contained high levels of reverse transcriptase activity (6). Analysis of the proteins synthesized in these strains, however, indicated that the major product was broken down into smaller species; partial purification of the soluble reverse transcriptase also indicated that multiple species were active. The breakdown of the fusion protein was not prevented by the addition of protease inhibitors in the lysis procedure (unpublished observations). An additional problem was that the majority of the fusion proteins partitioned into the insoluble fraction after cell lysis.

In an attempt to stabilize and solubilize the protein, deletions were made at the 3′ terminus of the cloned pol gene. The assumption was made that random Bal 31 deletions at this terminus might result in the formation of a protein that more closely resembled the authentic cleavage product, and might improve its stability in E. coli. To make deletions, plasmid pSHNB6 was linearized with Hind III, digested with Bal 31 nuclease for varying lengths of time, religated with T4 DNA ligase and used to transform E. coli HB101. Colonies were selected, and crude extracts were prepared and assayed for reverse transcriptase Table 2 summarizes the screening of colonies which were digested with Bal 31 nuclease for 7.5 and 15 minutes, producing an average deletion size of 200 and 400 bp, respectively. Since the deletions were bidirectional, the average number of base pairs removed from within the pol gene would be half of these numbers. The soluble reverse transcriptase activity of each colony produced after Bal 31 digestion for 7.5 minutes was similar to that of the parent plasmid pSHNB6. Colonies produced after digestion with Bal 31 nuclease for 15 minutes yielded a much larger range of activities. 10% of the colonies screened yielded no detectable reverse transcriptase activity, 45% of the colonies yielded less than 50% as much activity as the cells containing the parent pSHNB6 plasmid, and an additional 10% of the colonies yielded up to four-fold higher activity than the parent strain. The extracts from colonies which displayed enhanced reverse transcriptase activity were analyzed by polyacrylamide gel electrophoresis. One colony was selected for further study (pB6B15.23) because of the following features: (1) The specific activity of extracts from these cells was 3.5–4 times that of pSHNB6;(2) The level of induction was reproducible; (3) Coomassie blue staining of polyacrylamide gels indicated that a single species of $M_r=71,000$ was highly and stably overproduced; (4) Comparison of the insoluble and soluble fractions by polyacrylamide gel electrophoresis indicated that at least 30% of the $M_r=71,000$ band could be detected in the soluble fraction (data not shown).

The DNA sequence of this plasmid in the region of the deletion was determined and is shown at the bottom of FIG. 2. The deletion resulted in the removal of 204 nucleotides of the M-MuLV pol gene sequence and 64 bases of pATH1. The first stop codon is found twenty-seven bases from the new junction between the MuLV coding sequence and the vector. The carboxyl terminus of the fusion protein would contain nine novel amino acids encoded by the pBR322 sequence.

TABLE 2

| Summary of Bal 31 Deletion of pSHNB6 clone of MuLV Reverse Transcriptase | | | | | | |
|---|---|---|---|---|---|---|
| Time Bal 31 digestion (min) | Average deletion size | No. of colonies screened | % of pSHNB6 reverse transcriptase activity | | | |
| | | | 0–5 | 5–50 | 50–100 | 100 |
| | | | number of colonies | | | |
| 7.5 | 200 | 6 | 0 | 0 | 6 | 0 |
| 15 | 400 | 49 | 5 | 22 | 17 | 5 |

Summary of Bal 31 deletion of pSHNB6 clone of M-MuLV reverse transcriptase. Isolation of DNA fragments and subsequent Bal 31 nuclease digestion was as described in Experimental Procedures. The average deletion size was determined by electrophoresis of an aliquot of the reaction mixture on a 0.6% agarose gel in 90 mM Tris base, 90 mM Boric acid, and 2.5 mM EDTA. Extracts were prepared and assayed for reverse transcriptase as described in Experimental Procedures. Fractions were diluted (1:20) in Buffer M plus 0.2 M NaCl, assayed, and the level of activity was compared with the activity of the parent pSHNB6 construct. The entries in the table summarize three separate assays.

Analysis of the Fusion Proteins by Immune Precipitation

Analysis of crude extracts of cells carrying the pB6B15.23 plasmid by polyacrylamide gel electrophoresis and Coomassie blue stain indicated that a single stable fusion protein was synthesized. To determine if this was the only product made and if this product was structurally similar to the viral MuLV reverse transcriptase, immunoprecipitation was performed using various sera. Cultures of HB101 alone, HB101 bearing the vector plasmid pATH1, or HB101 bearing pB6B15.23, were grown with and without induction of the trp operon and were then labelled with ($^{35}$S) methionine. Extracts were prepared and were incubated with either normal goat serum; normal rabbit serum; two sera produced against authentic Rauscher MuLV reverse transcriptase, termed 775-424 and 775-454; and a serum specific for the N-terminus of the trpE protein. Immunoprecipitation of $^{35}$S-labelled extracts with various sera were performed as follows:

Preparation of $^{35}$S-labelled extracts, precipitation of $^{35}$S-labelled extracts, precipitation with various sera, and gel electrophoresis were as described in Experimental Procedures. The various sera used were as follows: Normal goat serum; Normal rabbit serum; Serum #775-424 (raised against Rauscher reverse transcriptase); Serum #775-454 (raised against Rauscher reverse transcriptase); Serum raised against the N-terminus of TRpE protein. A protein of $M_r=59,000$ was precipitated non-specifically with all the sera and extracts teste). Both anti-Rauscher reverse transcriptase sera recognized a single protein species of $M_r=71,000$ in the extracts of cells expressing the cloned M-MuLV reverse transcriptase. This protein was not present in HB101 or in HB101 bearing the parent plasmid pATH1. This unique protein species had the same electrophoretic mobility as the protein identified previously by Coomassie blue staining of crude extracts on polyacrylamide gels. Analysis of cells grown under conditions repressing the trp operon (in the presence of tryptophan and without the addition of indoleacrylic acid) indicated that lower levels of the $M_r=71,000$ species were being synthesized, although the protein could still be detected. The serum specific for the trpE protein recognized a $M_r=52,000$ species in HB101, presumed to be the trpE protein encoded by the chromosome (calculated $M_r=57,524$), as well as the truncated $M_r=37,000$ trpE protein encoded by pATH1. In extracts of HB101 containing pB6B15.23 grown under conditions of induction, only the $M_r=71,000$ fusion protein, which contains only the first eighteen amino acids of the trpE protein, was not recognized by this serum.

Purification of Reverse Transcriptase and Associated RNase H

To characterize the reverse transcriptase activity induced in cells carrying the pB6B15.23 plasmid, and to determine whether this activity did indeed reside in the novel pol-related protein, the activity was purified. The main assay for the enzyme measured the incorporation of radiolabelled dTTP into polymeric form on a poly(rA) template primed with oligo(dT). The crude extracts were prepared by detergent lysis after lysozyme treatment; the conditions of detergent and high salt utilized were important in solubilizing the activity. The presence of a nonionic detergent was required throughout the purification to prevent aggregation and loss of activity. The purification of the pB6B15.23 reverse transcriptase is detailed in the Experimental Procedures, and is summarized in Table 3. The final procedure involved column chromatography on DEAE-cellulose, phosphocellulose, polyribocytidylic acid-agarose, and hydroxylapatite.

The DEAE-cellulose step was used to remove nucleic acids from the preparation. Since the fusion protein did not bind DEAE-cellulose, only a modest purification of the enzyme was obtained by passing the activity through the column in a low salt concentration. Phosphocellulose column chromatography was the single most important step in the purification, resulting in a 6.6-fold increase in the specific activity of the preparation; the total recovery in this step was, unfortunately, rather low (24%). Polyribocytidylic acid chromatography was useful because very few proteins were capable of binding to the resin; the pB6B15.23 enzyme was essentially the only protein bound and eluted from the resin. Due to the high level of expression of the fusion protein in *E. coli*, the overall preparation of the reverse transcriptase activity required only a 22-fold purification.

The M-MuLV reverse transcriptase has been reported to have an associated RNase H activity (4,5). To determine if the region of the pol gene expressed in *E. coli* encoded the RNase H function, fractions from each stage

TABLE 3

Purification of pB6B15.23 Reverse Transcriptase and Associated Activities

| | Reverse Transcriptase | | | | RNase H | | | | |
| --- | --- | --- | --- | --- | --- | --- | --- | --- | --- |
| Fraction | Units/ml | Units | Yield % | Specific Activity Units/mg Protein | Units/ml | Units | Yield % | Specific Activity Units/mg Protein | Protein mg |
| DEAE load | 2643 | 629,200 | 100% | 737 | 225 | 53,500 | 100% | 62.7 | 854 |
| DEAE Flow through | 1400 | 490,000 | 78% | 972 | 31.6 | 11,060 | 21% | 21.9 | 504 |
| Phosphocellulose | 2786 | 118,420 | 19% | 6,440 | 52.2 | 2,218 | 4.1 | 121 | 18.4 |
| Poly C Agarose | 4918 | 56,510 | 9.0% | 12,840 | 62.2 | 715 | 1.3 | 163 | 4.4 |
| Hydroxylapatite | 15120 | 52,920 | 8.4% | 13,330 | 205 | 716 | 1.3 | 180 | 4.0 |

TABLE 3-continued

| | Purification of pB6B15.23 Reverse Transcriptase and Associated Activities | | | | | | | | |
|---|---|---|---|---|---|---|---|---|---|
| | Reverse Transcriptase | | | | RNase H | | | | |
| Fraction | Units/ml | Units | Yield % | Specific Activity Units/mg Protein | Units/ml | Units | Yield % | Specific Activity Units/mg Protein | Protein mg |
| Dialysis | 28910 | 50,590 | 8.0% | 16,160 | 297 | 519 | 0.97 | 166 | 3.1 |

Figure 4:
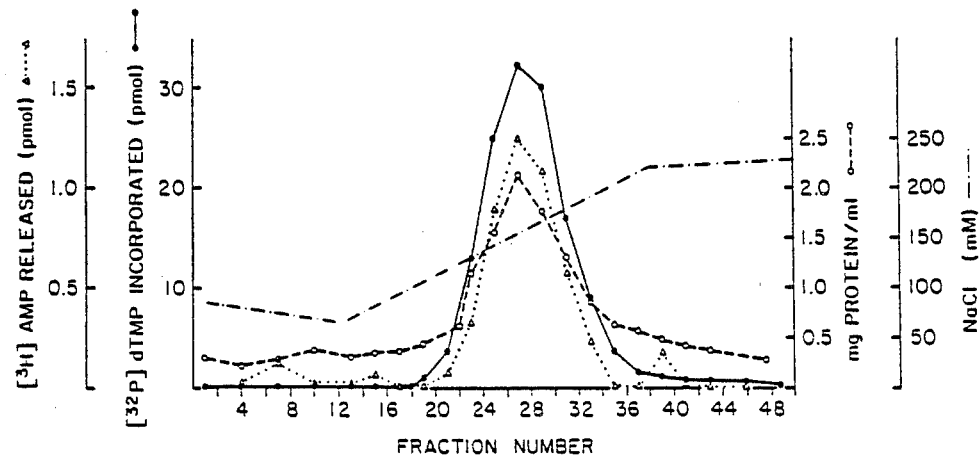
FIG. 4. Polyribocytidylic Acid-Agarose Chromatography The bound fraction from the phosphocellulose column was pooled, diluted, and applied to a polyribocytidylic acid-agarose column as described in the text. The column was washed and eluted with a salt gradient as indicated. Fractions were diluted (1:200) as described in FIG. 3. Reverse transcriptase (●—●) and RNase H (Δ—Δ) activities were assayed as described in Experimental Procedures in the presence of 1 μl and 3 μl of the diluted enzyme, respectively. Total protein (O —O) was determined using 10 μl of the column eluant as described in the Experimental Procedures.

Purification of pB6B15.23 reverse transcriptase and associated activities. Reverse transcriptase, RNase H, and total protein were assayed as described in Experimental Procedures. One unit of reverse transcriptase is defined as that amount of enzyme which will incorporate one nmol of ($^{32}$P) dTMP into a form retained on DE81 paper in 15 min. at 37° C. One unit of RNase H activity is defined as that amount of enzyme which will release one nmol of ($^3$H) AMP from an RNA:DNA hybrid into an acid soluble form in 30 min. at 37° C.

of the purification were assayed for RNase H as well as reverse transcriptase activity. The profile of these two activities on phosphocellulose chromatography is shown in FIG. 3. A substantial amount of RNAse H activity was eluted with low salt concentrations; in addition, a predominant peak of RNase H activity was coincident with the reverse transcriptase activity and eluted at 0.22 M NaCl. The RNase H activity eluting with the low salt concentration was not identified nor characterized further. The phosphocellulose fractions containing the reverse transcriptase activity and RNase H activity were further chromatographed on polyribocytidylic acid agarose (FIG. 4). The reverse transcriptase activity and the RNase H activity co-chromatographed as a single peak on this resin. These two activities were also associated after hydroxylapatite column chromatography and after glycerol gradient centrifugation in 0.5 M NaCl (see below). These results suggest that the central portion of the pol gene of M-MuLV present in the construct encodes both reverse transcriptase and RNase H activities.

Sodium Dodecyl Sulfate Gel Electrophoresis

To assess the purity of the reverse transcriptase, the protein fractions from the various stages of the purification were subjected to sodium dodecyl sulfate polyacrylamide gel electrophoresis, and the proteins were visualized by the silver staining procedure (10). pB6B15.23 reverse transcriptase was purified by sodium dodecyl sulfate-polyacrylamide gel electrophoresis. Samples from various stages of the purification were subjected to electrophoresis through a 10% polyacrylamide gel containing a 6% stacking gel followed by staining with silver as described (10). Samples were loaded which contained the following DEAE cellulose load; 18.1 µg protein, 10.6 units of enzyme. DEAE flow through fraction; 12.6 µg protein, 10.1 units of enzyme; pooled phosphocellulose preparation; 2.15 µg protein, 11.1 units of enzyme. Pooled polyribocytidylic acid-agarose preparation; 0.95 µg protein, 10.0 units of enzyme; pooled hydroxylapatite preparation; 1.03 µg protein, 10.8 units of enzyme; and final preparation after dialysis; 0.89 µg protein, 11.5 units of enzyme. The markers used were the $\beta$, $\beta'$, $\alpha$ and $\sigma$ subunit of E. coli RNA polymerase, myosin, $\beta$-galactosidase, albumin (bovine), albumin (egg), and carbonic anhydrase. The data presented the polypeptide composition of the material applied to the DEAE-cellulose column of the material that flowed through the DEAE-cellulose column of the pooled fractions after chromatography on phosphocellulose, polyribocytidylic acid-agarose, and hydroxylapatite; and of the final fraction. The analysis showed the presence of a single major band of $M_r=71,000$ in the late stages of the purification. Although the largest loss of reverse transcriptase activity occurred during phosphocellulose chromatography, extensive purification of the $M_r=71,000$ protein was achieved by this step. The $M_r=71,000$ protein is greater than 95% pure after polyribocytidylic acid-agarose chromatography. The hydroxylapatite chromatography and dialysis steps were mainly useful as a means of concentrating the protein.

Glycerol Gradient Centrifugation

Figure 5:
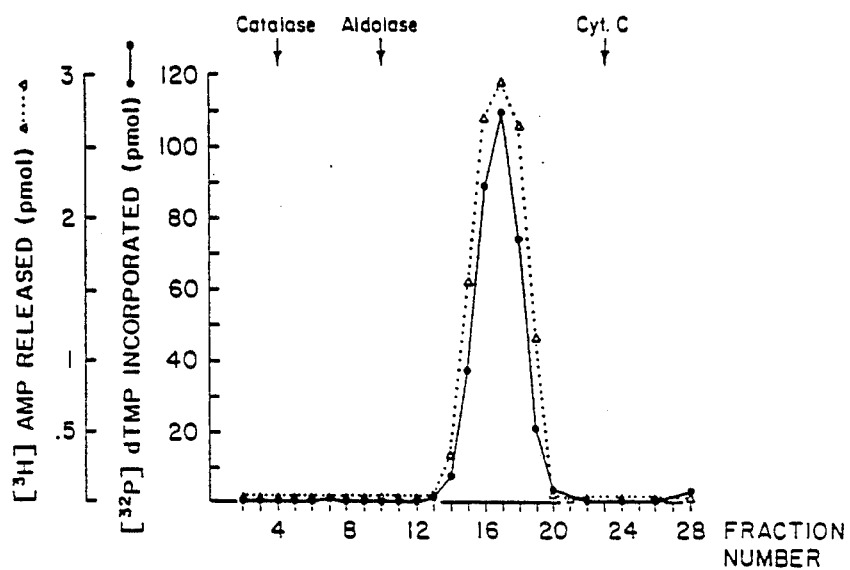
FIG. 5. Glycerol gradient centrifugation of reverse transcriptase fusion protein. 1445 units of pB6B15.23 reverse transcriptase (50 μl) was adjusted to final concentrations of 25 mM Tris-HCl, pH 7.9, 0.5 M NaCl, 1 mM dithiothreitol, 0.1 mM PMSF, 10% glycerol, and 0.02% Nonidet P40. An aliquot (200 μl) was layered onto a 4.8 ml linear gradient of 15–35% glycerol in the same buffer. The gradient was centrifuged for 24 h at 48,000 rpm in a Sorvall AH-650 rotor. Fractions (180 μl) were collected from the bottom of the tube, diluted 1:20 in Buffer M plus 0.2 M NaCl, and assayed for reverse transcriptase activities (1 and 3 μl/assay, respectively) as described in Experimental Procedures. Catalase, aldolase, and cytochrome C were sedimented in a parallel tube. The position of the markers were indicated by the arrows. Aliquots (5 μl) of fractions 13–21 were analyzed by electrophoresis through a sodium dodecyl sulfate polyacrylamide gel; and the proteins were stained with silver as described (10). The peptide composition of these fractions is shown beneath the graph. The position of migration and the $M_r$ of the marker proteins are indicated at the left and right of the gel.

To determine the subunit structure of the purified pB6B15.23 reverse transcriptase, the enzyme was further characterized by glycerol gradient sedimentation (FIG. 5). The reverse transcriptase and RNase H activities co-sedimented as a single peak with a sedimentation coefficient of 4.65S. Based on this sedimentation coefficient, the molecular mass of the species was estimated to be about 65,000 daltons. The proteins from the gradient fractions surrounding this peak of activity were subjected to sodium dodecyl sulfate polyacrylamide gel electrophoresis, and the proteins detected by silver stain. The results (FIG. 5) showed that the presence and intensity of the $M_r=71,000$ species parallelled the reverse transcriptase and associated RNase H profile. The purified fusion protein appears to behave as a monomer, as has been reported for the authentic M-MuLV reverse transcriptase (4,5).

Requirements for Reverse Transcriptase Activity of fusion Protein

The assay used for the purification of the pB6B15.23 reverse transcriptase activity measured the incorporation of dTMP on a poly (rA) template primed with oligo (dT). The requirements and the optimal conditions for DNA synthesis by the purified enzyme on this synthetic substrate were determined (Table 4, Section A). Under optimal conditions, incorporation of dTMP occurred linearly with time from 2 minutes to up to 2 h. Maximal DNA synthesis saturated at 500 pmols of dTMP incorporated, equivalent to one third of the available single stranded template. Incorporation was almost totally dependent on the presence of the template poly (rA) and primer oligo (dT). In addition, DNA synthesis required a divalent cation; either $Mn^{++}$ or $Mg^{++}$ were capable of supporting synthesis. The maximal incorporation occurred between 0.5–1.0 mM $MnCl_2$ and was greatly inhibited at levels higher than 2 mM (data not shown). $Mg^{++}$ supported DNA synthesis to a much lower

TABLE 4

| Requirements for pB6B15.23 MuLV Reverse Transcriptase | |
|---|---|
| | pmol ($^{32}$P) TMP incorporated |
| A. Additions | |
| Complete | 73 |
| Omit DTT | 80 |

TABLE 4-continued

Requirements for pB6B15.23 MuLV Reverse Transcriptase

| | | pmol ($^{32}$P) TMP incorporated |
|---|---|---|
| | Omit MnCl$_2$ | 0.2 |
| | Omit MnCl$_2$, Add MgCl$_2$ | 1.5 |
| | Add MgCl$_2$ | 70 |
| | Omit oligo (dT) | 1.3 |
| | Omit poly (rA) | 0.2 |
| B. | Preincubation | |
| | Complete | 50 |
| | Heated 37° C. 15 min. | 46 |
| | Proteinase K | 0.1 |
| | 10 mM N-Ethylmaleimide, plus 50 mM DTT | 0.5 |
| | 50 mM DTT, plus 10 mM N-Ethylmaleimide | 43 |
| | Heated 70° C., 15 min. | 0.1 |

Experiment A. The complete reaction mixture contained 50 mM Tris-HCl, pH 8.3, 20 mM dithiothreitol, 0.5 mM MnCl$_2$, 60 mM NaCl, 10 μg/ml oligo (dT), 20 μg/ml poly (rA), 20 μM dTTP (818 cpm/pmol), 0.1% NP40, and 0.072 unit of enzyme. Individual components were omitted as indicated. MgCl$_2$ was added at 0.5 mM concentration.
Experiment B. Complete reaction mixture was as described in experiment A. pB6B15.23 reverse transcriptase was diluted (1:400) in Buffer M plus 0.2 M NaCl and treated as described prior to the reverse transcriptase assay. 20 μl of enzyme was digested with proteinase K (5 μg) at 37° C. for 15 min. Treatment with N-ethylmaleimide and dithiothreitol was performed on ice for 15 min.

degree than Mn$^{++}$, with optimal activity occurring at 0.5 mM; higher concentration of Mg$^{++}$ also inhibited the reaction (data not shown). The addition of Mg$^{++}$ to a reaction mixture that already contained Mn$^{++}$, however, did not inhibit the Mn$^{++}$ dependent synthesis.

Maximal DNA synthesis on poly (rA): oligo (dT) occurred in the presence of 60–80 mM NaCl; standard reaction mixtures contained 60 mM NaCl. The effect of higher ionic strength is shown in Table 5, Section A. Inhibition of DNA synthesis occurred at 120 mM NaCl, with only 12% of the activity remaining at 240 mM NaCl. The enzyme activity was inhibited by inorganic phosphate at levels between 5 mM and 40 mM. The enzyme was extremely sensitive to pyrophosphate (Table 5, Section B); considerable inhibition of dTMP incorporation was seen at 0.1 mM NaPPi. Similar results were found when the concentration of free Mn$^{++}$ was maintained at 0.5 mM or at 1.0 mM in the reaction mixtures.

Omission of DTT from the reaction mixture appeared to slightly stimulate the reaction; however, the enzyme fraction contained 5 mM DTT, which may have partially compensated for this omission. The enzyme was almost completely inhibited in the presence of the sulfhydryl antagonist, N-ethylmaleimide (Table 4, Section B). This inhibition was completely prevented by the prior addition of dithiothreitol.

The final fraction was sensitive to preincubation with proteinase K as well as heating at 70° C. for 15 minutes. Heating at 42° C. for 15 minutes resulted in a 50% loss of activity (data not shown).

TABLE 5

Effects of Salt and Inhibitors of pB6B15.23 MuLV Reverse Transcriptase

| | | |
|---|---|---|
| A. | Complete | 125 |
| | Add 5 mM sodium phosphate | 91 |
| | Add 20 mM sodium phosphate | 58 |
| | Add 40 mM sodium phosphate | 17 |
| | Add NaCl, total 120 mM | 70 |
| | Add NaCl, total 180 mM | 45 |
| | Add NaCl, total 240 mM | 15 |
| B. | Complete | 99 |
| | Add 0.1 mM sodium pyrophosphate | 67 |
| | plus 0.1 mM MnCl$_2$ | |
| | Add 0.5 mM sodium pyrophosphate plus 0.5 mM MnCl$_2$ | 50 |
| | Add 1.0 mM sodium pyrophosphate plus 1.0 mM MnCl$_2$ | 6.4 |

Effect of salt and inhibitors of pB6B15.23 MuLV reverse transcriptase. Complete reaction mixture was as described in Table 4. Assay was performed as described in Experimental Procedures. The specific activity of ($\alpha^{32}$P) dTTP in Experiment A and B was 774 and 316 cpm/pmol, respectively.

Contaminating Activities

The purified enzyme preparation was assayed with ATPase activity in the absence and presence of single- and double-stranded DNA, and of poly rA: oligo dT, using ($\delta^{32}$P) ATP. No release ($^{32}$P) inorganic phosphate could be detected.

Fidelity of DNA synthesis

The assay measuring incorporation on the oligo (dT) and poly (rA) substrates was found to be totally dependent on template and primer (see above). To determine the fidelity of the template-directed synthesis, the incorporation of various ($\alpha^{32}$P) dNTPs was measured (Table 6). ($\alpha^{32}$P) dTTP was the only nucleotide with which significant incorporation could be detected. Since the authentic M-MuLV reverse transcriptase is capable of DNA-dependent DNA synthesis using an RNA primer, the possibility existed for the incorporation of dAMP: this would result from the use of the oligo (dT) as a template and the poly (rA) as the primer. The measured level of ($^{32}$P) dAMP incorporation was small and accounted for less than 0.1% of that observed with ($\alpha^{32}$P) dTTP In the presence of unlabelled dTTP, the level of misincorporation of ($^{32}$P) dCMP decreased, whereas a small increase of ($^{32}$P) dAMP incorporation was seen. The increase in dAMP incorporation may reflect a low level of second-strand DNA synthesis.

Synthesis of Long cDNA Products

In the viral life cycle, reverse transcriptase must synthesize double stranded DNA products over 8 kb in length (1, 24, 25). The size and nature of the cDNA

TABLE 6

Incorporation of various dNTPs

| dNTP | pmol ($^{32}$P) dNMP incorporated |
|---|---|
| ($\alpha^{32}$P) dTTP | 144 |
| ($\alpha^{32}$P) dCTP | 0.01 |
| ($\alpha^{32}$P) dGTP | 0.03 |
| ($\alpha^{32}$P) dATP | 0.16 |
| ($\alpha^{32}$P) dCTP plus TTP | 0.01 |
| ($\alpha^{32}$P) dGTP plus TTP | 0.01 |
| ($\alpha^{32}$P) dATP plus TTP | 0.19 |

Incorporation of various dNTPs. Assay was performed as described in Experimental Procedures. Labelled and unlabelled nucleoside triphosphates were added to 20 uM concentration. The specific activity of each ($\alpha^{32}$P) dNTP was: dTTP, 961 cpm/pmol; dCTP, 16,950 cpm/pmol; dGTP, 14,630 cpm/pmol; and dATP, 13,620 cpm/pmol.

products of pB6B15.23 reverse transcriptase were characterized using various poly A$^+$ mRNA preparations primed with oligo (dT). Reaction mixtures (30 μl) contained 100 mM Tris-HCl, pH 8.3, 10 mM MgCl$_2$, 2 mM dithiothreitol, 1 μg/ml oligo (dT), 200 μM dATP, dGTP, dATP, and dCTP (2160 cpm/pmol), 150 mM KCl, 0.05% Nonidet P40, and 60 ng of HOPCl poly A$^{(+)}$ RNA. pB6B15.23 reverse transcriptase was added as follows: 0.029 unit; 0.29 unit; 2.9 units; 29 units; 145 units; no enzyme addition; reaction in absence of RNA. Reaction mixtures were incubated at 37° C. for 1 h. and stopped by the addition of 20 μl of 2% sodium dodecyl sulfate, 50 mM EDA. 10 μg of carrier tRNA was added, and the mixture was extracted with phenol (50 μl), back extracted with H2O (25 μl), and ether extracted twice. Mixture was made 2 M in ammonium acetate and DNA products were precipitated after the addition of 2.5 volumes of ethanol. Pellets were resuspended in 2 M ammonium acetate (50 μl) and reprecipitated in 2.5 volumes of ethanol. Pellet was resuspended in 10 μl of 10 mM EDTA, and made 50 mM NaOH, 1 mM EDTA, 10% glycerol, in the presence of bromophenol blue, xylene cyanol, and bromocresol green indicator dyes. Samples were loaded onto a 1.2% agarose gel and electrophoresed for 14 h at 30 V in 30 mM NaOH, 1 mM EDTA. Gels were dried and subjected to autoradiography. ($\alpha^{32}P$) dNTPs were incorporated, and the DNA products were analyzed by electrophoresis through alkaline agarose gels and autoradiography. A titration of the enzyme on 60 ng of poly A+ RNA from HOPC myeloma cells, under conditions described for the avian reverse transcriptase, showed that the size of the DNA product depended dramatically on the amount of enzyme added. Little or no synthesis was detectable in the presence of 0.02–0.29 unit of enzyme. In the presence of 2.89 units of enzyme, the average DNA product was 365 bases long. When the amount of enzyme was increased ten fold, the DNA products were between 315 and 1900 bases in length; the prominent 1 kb species corresponds to the cDNA copy of the λ light chain mRNA. In the presence of still higher levels of enzyme, the size of the DNA product remained constant, indicating the absence of contaminating RNase. No DNA synthesis was detected in the absence of enzyme or template RNA.

Optimal conditions for synthesis with the pB6B15.23 reverse transcriptase were found by titrating the various components of the reaction. Both MgCl2 and MnCl2 could fulfill the divalent cation requirement at optimal concentrations of 10 mM and 6 mM, respectively. Maximal size and DNA synthesis occurred with a mixture of 8 mM MgCl2 and 4 mM MnCl2. At this level of divalent cations, the addition of 60 mM NaCl inhibited the DNA synthesis (data not shown). Efficient DNA synthesis occurred in the presence of high concentrations of deoxynucleoside triphosphates; reaction mixtures contained 2 mM of each dNTP.

Using the optimal conditions, cDNA was synthesized with an oligo (dT) primer on poly A+ RNA isolated from human fetal muscle tissue. This RNA preparation was chosen because it is presumably enriched for the very large (7 kb) myosin heavy chain mRNA; the size distribution of the product would therefore not be limited by the size of the RNA templates. Using a commercial preparation of the avian viral reverse transcriptase (20.8 units), the average size of the product was 1200–3300 bases.

The product was analyzed using human fetal muscle poly A$^{(+)}$ RNA template. Reaction mixtures (30 μl) contained 50 mM Tris-HCl, pH 8.3, 8 mM MgCl2, 4 mM MnCl2, 10 mM DTT, 1 μg/ml oligo (dT), 2 mM dCTP (1132 cpm/pmol), dGTP, dATP, and dTTP, 0.01% nonidet P40, and 1 μg of poly A $^{(+)}$ RNA isolated from human fetal muscle. Reverse transcriptase was added as follows: AMV reverse transcriptase, 21 units; pB6B15.23 reverse transcriptase 29 units; 87 units; 174 units; no enzyme addition; and 29 units in the absence of added RNA. Reactions were stopped and prepared for electrophoresis through 0.7% alkaline agarose gel as described in FIG. 3. The amount of sample and the exposure time of the individual lanes varied as followed: 40% of the sample was electrophoresed and the gel was exposed for 48 h; 60% of the sample was electrophoresed, gel was exposed for 12 h. One sample contained $^{32}P$-labeled HindIII digest of phage DNA. The product produced with 28.9, 86.7, and 173 units of pB6B15.23 reverse transcriptase. DNA synthesis saturated with 86.7 units of enzyme, and the majority of the DNA products were between 1.3 and 9.9 kilobases in length. The size distribution was not changed by the presence of excess enzyme, indicating that RNase contamination was negligible. DNA synthesis was not detected in the absence of RNA or reverse transcriptase.

To determine whether the products were single-stranded copies of the mRNAs or double-stranded molecules resulting from hairpin loopbacks serving as primers, cDNA synthesis was performed on poly A+ mRNA isolated from human reticulocyte lysates.

Product analysis using human reticulocyte poly A$^{(+)}$ RNA as template was performed as follows: Poly A$^{(+)}$ RNA from human reticulocyte was isolated as described in Experimental Procedures. Reaction mixtures containing approximately 0.2 μg of RNA were assembled as described in above Actinomycin D (0.5 μl in ethanol) was added to 100 μg/ml where indicated. Samples were electrophoresed through a 1.2% alkaline agarose gel. The samples were as follows product of AMV reverse transcriptase; (a) 2.1 units; (b) 21 units; (c) product of pB6B15.23 reverse transcriptase (d) 21 units; (e) 87 units; (f) 29 units plus actin D, (g) 87 units plus actinomycin D, (h) no enzyme addition, and (i) 29 units enzyme in absence of RNA. (j) marker $^{32}P$-labeled HindIII fragments of phage Exposure (a) and (b) was 12 h, and (c)–(d) exposed 24 h. The predominant species in these preparations are mRNAs of about 570 and 640 nucleotides, encoding the α and β-globins. Synthesis with low levels of avian reverse transcriptase yielded a single major product approximately 600 bases in length, corresponding to the full-length single-stranded cDNA species synthesis at high levels yielded predominantly two DNA species approximately 600 and 1200 bases in length, corresponding to the single- and double-stranded cDNAs; the major product was the smaller, single-stranded cDNA copy. Synthesis with low levels of the purified pB6B15.23 reverse transcriptase also yielded the single-stranded product. With high levels of the enzyme, the 1200 base products were the predominant species, and the single strand products were not detected as a discrete species, indicating that after the completion of the full-length first strand, the DNA was efficiently looped back and used as a primer for the second-strand synthesis. To confirm that the 1200-base products were in fact the result of second-strand synthesis, DNA synthesis was performed in the presence of actinomycin D. Actinomycin D binds preferentially to double-stranded nucleic acids and therefore inhibits the second strand synthesis. The major products of cDNA synthesis of reticulocyte polyA+ RNA with pB6B15.23 reverse transcriptase in the presence of actinomycin D were the 600 base species. No products larger than this species could be detected. As before, no products were synthesized in the absence of RNA or enzyme.

DISCUSSION

These experiments show that a gene fusion containing a portion of the bacterial trpE gene and the central portion of the M-MuLV pol gene can induce the synthesis of a stable protein with high levels of reverse transcriptase activity. A critical step in the successful expression of this activity was the screening of numerous variants of our initial gene constructs for the formation of maximum levels of stable, soluble protein. Although our initial clone did induce considerable reverse transcriptase activity (6), the fusion protein was exceedingly unstable, and the large primary translation product was reproducibly cleaved into several distinct proteolytic products. The distribution of those species into soluble and insoluble fractions showed that the smaller products were more soluble than the larger ones. The approach taken to counter these problems, therefore, was to generate deletions in the DNA which removed unnecessary codons, and to screen the variants for maximal activity. This procedure resulted in the isolation of a construct that overproduced an extremely stable, soluble, and active fusion protein This approach may be of general use in maximizing soluble activity of a variety of proteins expressed in E. coli.

The reverse transcriptase fusion protein required a 22-fold purification to yield a nearly homogeneous enzyme preparation. The purification scheme involved multiple column chromatography steps, including polyribocytidylic acid-agarose. This resin has been used for the rapid method of purification of RNA dependent-DNA polymerase from avian myeloblastosis virions (33). The results described in this paper showed that this affinity column was useful as well for the rapid purification of reverse transcriptase activities expressed in E. coli.

New information has been obtained about the various functional domains of the pol gene through its expression in E. coli. The expression of the pol gene from nucleotide position 2574–4588 (8) confirms that both the reverse transcriptase and RNase H activities are encoded by this region and can coexist in a single protein species of $M_r=71,000$. Neither activity required the exact viral termini, since the N-terminus of the fusion protein is encoded by the trpE gene and the C-terminus contains nine random amino acids encoded by pBR322 sequences. Analysis of clones showed that a deletion 140 base pairs larger than that in pB6B15.23 (up to the BglII site) still did not abolish reverse transcriptase activity.

Due to the difficulty in obtaining large quantities of the authentic M-MuLV reverse transcriptase, direct comparison between the pB6B15.23 enzyme and the authentic enzyme could not be made. Data previously published on the viral enzyme indicates that the pB6B15.23 reverse transcriptase was identical to its viral counterpart in its optimal conditions for synthesis on poly (rA): oligo (dT) (4,18,34). The sedimentation coefficients determined by glycerol gradient centrifugation also showed that both the viral and the cloned enzyme were monomers (4,5). The major difference detected between the viral protein and pB6B15.23 reverse transcriptase was the low activity of the pB6B15.23 enzyme on poly (rA): oligo (dT) in the presence of $Mn^{++}$ vs. $Mg^{++}$ for the authentic viral protein was reported to be 3.5:1 (4), whereas for pB6B15.23 reverse transcriptase, this ratio was 49:1.

The structure of the reverse transcriptase from avian retroviruses is quite different from that of the murine viruses. The predominant functional form of the avian enzyme is a heterodimer of two subunits (35), alpha and beta; the larger beta subunit is cleaved in the virion to form the smaller alpha subunit and a third protein, pp32, exhibiting DNA endonuclease activity (36,37,38). The enzymatic properties of the avian enzyme is also quite different from those of the pB6B15.23 enzyme. Published protocols, for example, have suggested that the addition of NaPPi (39) and synthesis at elevated temperatures (40) were suitable for the formation of full-length products using the avian enzyme; we found that the bacterial enzyme, in contrast, was very sensitive to NaPPi and lost 50% of its activity in 15 minutes when incubated at 42° C. An additional difference between the avian and the pB6B15.23 enzyme was that the avian enzyme formed double-stranded cDNAs only poorly, while the bacterial reverse transcriptase was found to efficiently catalyze hairpin synthesis on DNA to form double stranded DNA products. Actinomycin D inhibited double stranded DNA synthesis and limited synthesis to the first strand, as with known DNA polymerases.

On a natural RNA template, the size of the DNA product was found to increase with increasing concentration of the cloned M-MuLV reverse transcriptase; under optimal conditions, the enzyme could synthesize cDNAs up to 9.9 kb long. Maximal DNA synthesis using the polyA+ mRNA from human fetal muscle tissue occurred when the protein was present at a 4.5-fold excess over the RNA (w/w), or approximately one molecule of protein every 48 nucleotides; it is not known, however, what fraction of the reverse transcriptase molecules are active.

Further studies in this laboratory will focus on generating temperature sensitive mutuants of the reverse transcriptase and RNase H activities. These mutants will be isolated by mutagenesis of the cloned MuLV reverse transcriptase; the effects of the mutations will be analyzed after transfer of the altered DNA back into the viral genome and recovery of virus. We hope that analysis of such mutants will result in a better understanding of the role of the activities of the enzyme in the viral life cycle and the interactions of the protein with the other viral gene products.

REFERENCES

1. Varmus, H., and Swanstrom, R. (1982) in *RNA Tumor Viruses* (R. Weiss, N. Teich, H. Varmus, and J. Coffin, eds) pp. 369–512. Cold Spring Harbor, New York.

2. Witte, O. N., and Baltimore, D. (1978) *J. Virol* 26, 750–761.

3. Kopchik, J. J., Karshin, W. L., and Arlinghaus, R. B. (1979) *J. Virol* 30, 610–623. 4. Verma, I. M. (1975) *J. Virol* 15, 843–854.

5. Gerard, G. F., and Grandgenett, D. P. (1975) *J. Virol* 15, 785–797.

6. Tanese, N., Roth, M., and Goff, S. P. (1985) *Proc. Natl. Acad. Sci.,* in press.

7. Sutcliffe, J. G. (1979) *Cold Spring Harb Symp Ouant Biol* 43, 77–85.

8. Sutcliffe, J. G. (1978) *Cold Spring Harb Symp Ouant Biol* 43, 77–90.

9. Maxam, A., & Gilbert, W. (1980) *Meth. Enzymology* 65, 499–599.

10. Oakley, B., Kirsch, D., and Morris R. (1980) *Anal Biochem* 105, 361–363.

11. Boyer, H. W., & Roulland-Dussouix, D. (1969) *J. Mol. Biol.* 41, 459–472.

12. Kleid, D. G., Yansura, D., Small, B., Dowbenko, D., Moore, D. M., Grubman, M. J., McKercher, P. D., Morgan, D. O., Robertson, B. H , & Bachrach, H. L. (1981) *Science* 214, 1125–1129.

13. Miller, J. H. (1972) in Experiments in Molecular Genetics, Cold Spring Harbor Press, p. 431.

14. Schwartzberg, P., Colicelli, J., & Goff, S. P. (1983) *J. Virol.* 46, 538–546.

15. Lobel, L. I., & Goff, S. P. (1984) *Proc. Natl. Acad. Sci. USA* 81, 4149–4153.

16. Crawford, S., & Goff, S. P. (1985) *J. Virol.* 53, 899–907.

17. Schwartzberg, P., Colicelli, J., & Goff, S. P. (1984) *Cell* 37, 1043–1052.

18. Goff, S. P., Traktman, P., & Baltimore, D. (1981) *J. Virol.* 38, 239–248.

19. Karkas, J. D. (1973) *Proc. Natl. Acad. Sci. USA* 70, 3834–3838.

20. Gefter, M. L , Hirota, Y., Kornberg, T., Wechsler, J. A., & Barnoux, C. (1971) *Proc. Natl. Acad. Sci. USA* 68, 3150–3154.

21. Campbell, J. L., Soll, L., & Richardson, C. C. (1972) *Proc. Natl. Acad. Sci. USA* 69, 2090–2094.

22. Spindler, K. R., Rosser, D. S. E., & Berk, A. J. (1984) *J. Virol.* 49, 132–141.

23. Richardson, C , Schildkraut, C. L., Aposhian, H. V., & Kornberg, A. (1964) *J. Biol. Chem.* 239, 222.

24. Wagner, A. F., Bugianesi, R. L., and Shen, T. Y. (1971) *Biochem Biophys Res Comm* 45, 184–189.

25. Burgess, R. R., and Jendrisak, J. J. (1975) *Biochem* 14, 4634–4938.

26. Gonzalez, N., Wiggs, J., and Chamberlain, M. J. (1977), *Arch Biochem Biophys* 182, 404–408.

27. Bradford, M. (1976) *Anal Biochem* 72, 248–254.

28. Chirgwin, J. M., Przybyla, A. E., MacDonald, R. J., and Rutter, W. J. (1979) *Biochem* 18, 5294–5299.

29. Katz, L., Kingsbury, D. T., and Helsinki, D. R. (1973) *J Bacteriol* 114, 577–591.

30. Vogelstein, B., & Gillespie, D. (1979) *Proc. Natl. Acad. Sci. USA* 76, 615–619.

31. Mandel, M. & Higa, A. (1970) *J. Mol. Biol.* 53, 159–162.

32. Birnbaim, H. C., and Doly, J. (1979), *Nucl Acid Res* 7, 1513–1523.

33. Marcus, S. L. Modak, M. J., and Cavalieri, L. F. (1974) *J Virol* 14, 853–859.

34. Baltimore, D., and Smoler, D. (1971) *Proc Natl Acad Sci USA* 68, 1507–1511.

35. Grandgenett, D. P., Gerard, G. F., and Green, M. (1973) *Proc Natl Acad Sci USA* 70, 230–234.

36. Grandgenett, D. P., Golumb, M., and Vora, A. C. (1980) *J Virol* 33. 264–271.

37. Verma, I. M. (1977) *Biochem Biophys Acta* 473, 1–28.

38. Misra, T. K., Grandgenett, D. P., and Parsons, J. T. (1982) *J Virol* 44, 330–343.

39. Kacian, D. L., and Myers, J. C. (1976) *Proc Natl Acad Sci USA* 73, 2191–2195.

40. Retzel, E. F., Collet, M. S., and Faras, A. J. (1980) *Biochem.* 19, 513–518.

What is claimed is:

1. A plasmid designated pB6B15.23 having the restriction map shown in FIG. 2 and deposited in *Escherichia coli* HB101 under ATCC Accession No. 39939.

2. An *Escherichia coli* HB101 cell which contains the plasmid of claim 1 and which is deposited under ATCC Accession No. 39939.

3. A method for producing a polypeptide having reverse transcriptase activity which comprises growing the *Escherichia coli* HB101 cell of claim 2 under suitable conditions permitting production of the polypeptide and recovering the polypeptide so produced.

* * * * *